US012599311B2

(12) United States Patent
Davies et al.

(10) Patent No.: US 12,599,311 B2
(45) Date of Patent: Apr. 14, 2026

(54) DEVICE FOR MEASURING A PRESSURE DIFFERENTIAL

(71) Applicant: Clinical Technology Limited, Leeds (GB)

(72) Inventors: Gwilym Alban Davies, Leeds (GB); Brian Stewart Hoyle, Leeds (GB)

(73) Assignee: Clinical Technology Limited, Leeds (GB)

( * ) Notice: Subject to any disclaimer, the term of this patent is extended or adjusted under 35 U.S.C. 154(b) by 624 days.

(21) Appl. No.: 17/920,905

(22) PCT Filed: Apr. 23, 2021

(86) PCT No.: PCT/GB2021/050995
§ 371 (c)(1),
(2) Date: Oct. 24, 2022

(87) PCT Pub. No.: WO2021/214489
PCT Pub. Date: Oct. 28, 2021

(65) Prior Publication Data
US 2023/0181054 A1 Jun. 15, 2023

(30) Foreign Application Priority Data

Apr. 24, 2020 (GB) ..................................... 2006020

(51) Int. Cl.
*A61B 5/03* (2006.01)
*A61B 5/00* (2006.01)
(52) U.S. Cl.
CPC ............ *A61B 5/036* (2013.01); *A61B 5/6848* (2013.01); *A61B 2560/0223* (2013.01); *A61B 2562/0247* (2013.01); *A61B 2562/028* (2013.01)

(58) Field of Classification Search
CPC .......... A61B 2562/0247; A61B 5/0215; A61B 5/6848; A61B 5/036; G01L 13/06
See application file for complete search history.

(56) References Cited

U.S. PATENT DOCUMENTS 3,553,625 A 1/1971 Stedman
3,703,099 A 11/1972 Rouse
(Continued)

*Primary Examiner* — Etsub D Berhanu
*Assistant Examiner* — Janki M Bava
(74) *Attorney, Agent, or Firm* — Joseph C. Zucchero; Carolyn S. Elmore; Elmore Patent Law Group, P.C.

(57) ABSTRACT

A device for measuring a pressure differential comprises a tube, at least one pressure sensor and a processor. The tube comprises a closed insertion portion for insertion into a body, the insertion portion having an insertion end and an internal bore in communication with ambient pressure via an opening in the tube. The sensor is located in or on the insertion portion and comprises an internally facing region in communication with the bore and an externally facing region in communication with an exterior of the tube. The processor is configured to provide a stimulus, which may be an electrical stimulus, to the pressure sensor so that when the stimulus is provided, the pressure sensor provides a measurable response wherein the processor correlates the response with the pressure differential between the exterior of the tube and the bore. The measurable response may be indicative of a change in pressure differential between the exterior of the tube and the bore. There may be a plurality of pressure sensors, in which case at least two of the sensors may have different resonant frequencies at the same pressure differential. The insertion portion may comprise at least one aperture sealed by at least one pressure sensor. The pressure sensor may comprise an electromechanical or micro-electromechanical material and may comprises a piezoelectric
(Continued)

Plan view
Pressure sensor ~3 x 1mm Active CSA
Solid tipped 14G needle - ID 1.6mm, OD 2.1mm and/or electrocapacitive sensor. The externally facing region of the pressure sensor may comprise a coating, which may be electrically insulative.

20 Claims, 9 Drawing Sheets

(56) References Cited

U.S. PATENT DOCUMENTS

| | | | |
|---|---|---|---|
| 4,886,070 A | 12/1989 | Demarest | |
| 2014/0288459 A1 | 9/2014 | Yadav et al. | |
| 2018/0168460 A1* | 6/2018 | Morris ................. | A61B 5/0215 |

* cited by examiner

Side elevation

Plan view

Pressure sensor ~3 x 1mm Active CSA

Solid tipped 14G needle - ID 1.6mm, OD 2.1mm

Thumb grip 30

Display 32

Needle 12

24 Sensor unit inserted into 5mm milled slot

Contact wires routed through needle bore

Sensor (3mm x ~1mm) active surface with underside coating

Sensor unit having 5mm x 1.6mm curved top for insertion and cementing into slot giving smooth sensor surface CP trend Flashing at detected 'pulse rate' or 'x' if none Compartment Pressure

34

CP:20mmHg Pulse 60:75% o Mode:E/M

Needle 12

Mode indication

Thumb grip
30

32

Pulse rate and %tage Relative Amplitude (??)

210

214

244

Depth scale 242

Lock tab 246

12

Legs (2) 238

Pedestal 236

Fixing tab(4)
248

DEVICE FOR MEASURING A PRESSURE DIFFERENTIAL

FIELD OF THE INVENTION

The present invention relates to a device for measuring a pressure differential, and to associated methods of measuring a pressure differential.

BACKGROUND OF THE INVENTION

Compartments are regions within a human or animal body that are enclosed within connective fascia tissue. Compartment syndrome (CS) is a state of tissue swelling and increased pressure within a compartment. An elevated compartment pressure may oppose normal perfusion, which may cause disrupted blood supply associated with tissue necrosis and nerve damage. The pressure in a compartment may be a "static" pressure. That is, the pressure may be relatively constant over reasonable time intervals.

CS may be acute or may be chronic (also known as exertional compartment syndrome). Acute compartment syndrome is typically associated with trauma to the affected compartment, such as in fractures or muscle injuries. Exertional compartment syndrome is often associated with repeated microtrauma related to physical activity.

To facilitate recovery from compartment syndrome, a diagnosis must be made quickly and accurately. A clinical diagnosis of compartment syndrome is determined by measuring the relevant compartment pressure in a patient. If diagnosed promptly, a fasciotomy operation may be performed to remove seriously affected tissue, release the tissue pressure in the compartment, and later to close the surgical wound. Clinical indications for fasciotomy vary between authorities, however, in the UK a fasciotomy is required if:

(i) the compartment pressure is greater than 30-40 mmHg; or (ii) the pressure difference between diastolic pressure and the compartment pressure is less than 30 mmHg.

A fasciotomy is a major surgical procedure with an extended period of recovery (typically totalling several months) including considerable follow-up healthcare, and may lead to scarring. A false positive diagnosis (i.e. a diagnosis of CS made when there is no CS) results in needless operation, unnecessary costs of aftercare, and subjects the patient to additional risk and morbidity. It is therefore desirable to reduce the occurrence of false positive diagnoses.

On the other hand, if a false negative diagnosis is made, the diagnosis of CS may be delayed, or worse, remain undiagnosed and untreated. If a diagnosis of CS is delayed, it may be necessary to perform an even more severe (acute) surgical procedure, which may necessitate amputation of the relevant body part, for example, amputation of a leg. Worse still, if CS is left undiagnosed and untreated, the condition can be fatal. A false negative diagnosis may further lead to the relevant healthcare provider to be subject to litigation and compensation costs. It is therefore highly desirable to avoid false negative diagnoses.

The time available for prompt diagnosis is limited to a few hours, after which the more extreme measures are likely to be the only option to save the life of the patient.

Known devices for measuring compartment pressure comprise a needle connected to a manometer line, or a column of fluid. A known device, described in U.S. Pat. No. 4,817,629, comprises a syringe, a pressure chamber having a flexible diaphragm, and means to penetrate the skin of the patient. The known device must be purged of air and calibrated (or zeroed) prior to insertion into the patient. It is necessary to zero known devices at an angle approximating the final angle of the device after introduction of the needle into the compartment or tissues. If the device is not fully purged of air, zeroed in this manner or if the angle of the device is varied, the measured pressures may not be accurate. An inaccurate pressure measurement could lead to either a false positive or a false negative diagnosis. It is desirable to improve the accuracy and reliability of a pressure monitoring device. It is also desirable to simplify the calibration process of a pressure monitoring device.

Exertional (or chronic) CS occurs in patients undertaking activity or exercise. Compartment pressure measurement should be performed during activity for a definitive diagnosis. However, since known devices require the measurement step to be performed at the same angle as the calibration step, known devices are not suitable to measure compartment pressures during activity as errors may be introduced into the measurement if the patient moves. It is desirable to provide a reliable measurement of compartment pressures during activity (i.e. whilst the patient is moving).

In addition to measuring "static" pressures, it is also useful to measure and monitor "dynamic" pressure levels. A "dynamic" pressure has a value that is continuously varying, for example changes in arterial pressure caused by the cardiac cycle.

Cardiac procedures are intimately concerned with blood pressure levels in vascular structures and in one or more chambers of the heart during a cardiac procedure, and in following post-operative care. A typical management practice is to introduce one or several narrow bore manometer tubes at key points to allow local pressure at the open end of each tube to be measured. Under ideal conditions, this conventional arrangement provides the capability to sense local pressures. However, in practice there may be significant problems. In particular the tube can become blocked or contain one or more air bubbles. In either case this prevents the manometer line from providing an accurate pressure reading. It is desirable for a device to measure pressure levels with improved sensitivity. It is desirable for a device to be suitable for providing these measurements over an extended period of time without degradation or drift in measurements.

Cerebral injuries are typically followed by surgery to arrest suspected internal bleeding. Clinicians must then monitor any internal swelling of brain tissue which is normally covered in cerebrospinal fluid (CSF). Swelling can cause internal pressure within the skull resulting in lowered or disrupted blood supply and consequently can lead to major damage, and possible permanent impairment. A typical management practice is to introduce a narrow bore manometer tube which allows the pressure of the local CSF to be measured. The tube is arranged to be left in place and the wound closure is completed and sealed by the use of a purse suture tightened around the line tube. When the danger of swelling has passed the tube can be withdrawn and the purse suture closed.

Under ideal conditions, this conventional arrangement provides the capability to sense the pressure of local CSF. However, in practice it has significant problems. In particular, the tube can become blocked or filled with air bubbles. In either case this prevents the manometer line from providing an accurate pressure reading.

It will be appreciated that, in addition to the specific problems described above, there is a general desire and need to develop a device that quickly, accurately and reliably measures static and/or dynamic pressures in a body, particularly compartment pressures. It is desirable to measure the static compartment pressure value. It is desirable to measure exertional compartment pressure, or compartment pressure changes during activity. It is further desirable to measure local dynamic variation in pressure arising from the cardiac cycle. Such a device could assist clinicians making a speedy and reliable diagnosis of compartment syndrome, thereby reducing false negative and false positive diagnoses. Such a device could help clinicians to make a true positive diagnosis, which could lead to a life-saving operation. Such a device could help clinicians to make a true negative diagnosis, which could avoid unnecessary operation, expense, extended period of hospitalisation and/or scarring for the patient. Such a device could also help to monitor internal cerebrospinal fluid pressure during head trauma surgery and in postoperative care. Such a device could also help to monitor internal blood pressure levels conditions during cardiac procedures and in postoperative care. Such a device could also support clinicians in the diagnosis and monitoring of a range of other medical conditions that may occur in clinical practice where there is a critical need to sense or measure internal pressures within the body. The present invention, in at least some of its embodiments, seeks to address at least some of these problems, desires and needs.

SUMMARY OF THE INVENTION

According to a first aspect of the invention there is a device for measuring a pressure differential comprising:

a tube comprising a closed insertion portion for insertion into a body, the insertion portion having an insertion end, and an internal bore which is in communication with ambient pressure via an opening in the tube, at least one pressure sensor located in or on the insertion portion, the pressure sensor comprising an internally facing region which is in communication with the internal bore and an externally facing region which is in communication with an exterior of the tube; and a processor configured to provide a stimulus to the pressure sensor so that when the stimulus is provided, the pressure sensor provides a measurable response, wherein the processor correlates the measurable response with the pressure differential between the exterior of the tube and the internal bore.

The device of the present invention has major advantages. For example, the closed insertion portion prevents the internal bore from becoming blocked, and also prevents air bubbles from entering the internal bore. A closed insertion portion may facilitate sterilisation and provide fewer sites for bacterial growth. The closed insertion portion may allow the device to be re-used with a lower risk of infection or spread of infection. Further, the presence of air bubbles does not affect the pressure measurement. This helps to improve the reliability of the pressure measurement and can help to reduce the risks of infection. The device may self-calibrate, for example, by virtue of the internal bore being in communication with ambient pressure. The device may be suitable to provide reliable pressure measurements even when the body is moving or active.

The pressure differential may be a change in pressure differential. The internally facing region is in communication with ambient pressure via the internal bore. The exterior of the tube is in communication with an external pressure.

Typically, the ambient pressure that the internal bore is in communication with is atmospheric pressure. Alternatively, the internal bore may be sealed and maintained at a fixed reference pressure. Measuring a pressure differential in respect of ambient pressure allows the device to self-calibrate and allows the pressure differential to be measured without using balanced hydraulics, manometer lines, and the like. Changes in atmospheric pressure may affect the pressure exterior of the tube and the pressure within the internal bore equally.

The tube may be a needle. The tube may be a hypodermic needle. The tube may be a lancet.

The insertion portion may be rigid. The tube may be rigid. The tube may be made from a metal, such as steel.

Alternatively, the insertion portion may be flexible. The tube may be flexible. A flexible tube or insertion portion may facilitate insertion and positioning of the insertion portion. The tube may be made from a polymer, such as plastic.

The tube may be constructed of several sections made of different materials. A section may be rigid. A section may be flexible. A rigid section may be a needle for penetration. Another section may be flexible for the convenient coupling to monitoring equipment. The sections may be joined to ensure that the integrity of the internal tube pressure is maintained.

Preferably, all sections of the tube may have a wall thickness sufficient to withstand the expected pressure within the body. This helps the insertion portion to maintain the diameter of the internal bore, so that the internal bore maintains communication with ambient pressure during and after insertion into a body. Preferably, the tube may be resistant to kinking so that the communication between the internal bore and ambient pressure is not obstructed inadvertently.

The insertion end may comprise a sharp tip. A sharp tip advantageously facilitates insertion of the insertion end into a body where appropriate by penetration.

The insertion end may have a rounded tip. The insertion end may have a blunt tip. A blunt or rounded tip advantageously facilitates insertion into a body where appropriate, via a blood vessel for positioning within a cavity of the body such as a chamber of the heart, or when positioned by a surgeon before closing a surgery site using a purse suture or similar method to allow later removal after postoperative monitoring.

The at least one pressure sensor may be located proximal to the insertion end. Locating the at least one pressure sensor proximal to the insertion end minimises the tube penetration depth required for pressure measurement. The term proximal is used here to mean closer to the insertion end than to the opening.

The device may comprise a plurality of pressure sensors. The plurality of pressure sensors may be an array of pressure sensors. The plurality of pressure sensors may be arranged radially around the tube. The plurality of pressure sensors may be arranged axially along the tube.

The at least one pressure sensor may have a resonant frequency. The resonant frequency of the at least one pressure sensor may correspond to the pressure differential between the exterior of the tube and the internal bore. The stimulus may cause at least one pressure sensor to resonate, for example, at its resonant frequency. When mechanically excited (e.g. when the stimulus is provided), the at least one pressure sensor may exhibit a resonant frequency dependent upon the differential pressure. At least two of the pressure sensors may have different resonant frequencies at the same pressure differential. The resonant frequency of each pressure sensor may depend on the pressure differential between the exterior of the tube and the internal bore. At least two of the pressure sensors may resonate at the same resonant frequency at different pressure differentials. That is, a first pressure sensor may resonate at a first resonant frequency at a first pressure differential; and a second pressure sensor may resonate at the first resonant frequency at a second pressure differential, wherein the second pressure differential is greater than the first pressure differential. The resonant frequency of each pressure sensor may be tuned to resonate at a desired resonant frequency.

The externally facing region of the pressure sensor may be substantially aligned (or flush) with the exterior of the tube. The pressure sensor may be shaped to substantially correspond to the profile of the exterior of the tube. For example, for a cylindrical tube, the externally facing region of the pressure sensor may be curved to match the cylindrical profile of the tube.

The insertion portion may comprise at least one sealed aperture, in which each aperture is sealed by at least one pressure sensor. The sealed aperture may be sealed by two or more pressure sensors. The aperture may be a slot in the insertion portion. The aperture may be milled or machined into the insertion portion. The at least one aperture may be a plurality of apertures. The plurality of apertures may be arranged radially around the tube. The plurality of apertures may be arranged axially along the tube. Each aperture may be sealed by two or more of the pressure sensors. Arranging the pressure sensor in an aperture or slot may beneficially cause the pressure sensor to be pressed against the insertion portion when the insertion portion is inserted into a body, for example, if the body has a higher pressure relative to the ambient pressure. This maintains the seal between the insertion portion and the pressure sensor, and helps to prevent the pressure sensor from being dislodged from the aperture during insertion. The pressure sensor may be mounted on a mounting surface, such as a mounting membrane, across the aperture. The mounting surface may be suitable for deflecting or flexing when the pressure sensor is provided with the stimulus. For example, the mounting surface may deflect or flex when the pressure sensor is vibrating, such as vibrating in a mechanical resonance.

The at least one pressure sensor may comprise an electro-mechanical material or any other suitable material. The at least one pressure sensor may be a transducer.

The at least one pressure sensor may comprise a piezo-electric pressure sensor. A piezoelectric pressure sensor may respond to an applied electrical stimulus to provide a mechanical resonance. This resonance may provide a measurable frequency response. The measurable frequency response may be correlated to the pressure differential between the exterior of the tube and the internal bore. This may be a static of dynamic pressure. For example, through calibration a measurable frequency response may be indicative of "static" pressure (i.e. a relatively constant pressure). A piezoelectric pressure sensor may respond to a changing external physical or mechanical stimulus to provide an electro-motive force. The external stimulus may be an applied stress caused from a changing pressure differential across the pressure sensor. By way of example, through calibration an electro-motive force response of sequential temporal samples may be indicative of "dynamic" pressure (i.e. a changing pressure).

The at least one pressure sensor may comprise an electro-capacitive pressure sensor. The electro-capacitive pressure sensor may comprise a capacitive element. The capacitive element may comprise at least two electrodes. The at least two electrodes may be displaceable relative to each other. A first electrode may be fixed and an adjacent electrode may have mechanical freedom to be displaced relative to the first electrode. The at least two electrodes may be mounted such that parts may have mechanical freedom to be relatively displaced. When a capacitor is charged, the resulting electrostatic field produces a force between the electrodes that tends to push them apart (to minimise the stored energy). If at least one electrode is flexible, a motion will result. When a stimulus, such as an AC electrical stimulus, is provided to an electro-capacitive pressure sensor, the electro-capacitive pressure sensor may vibrate, for example, to generate ultrasound. The electro-capacitive pressure sensor may comprise a capacitive micromachined ultrasonic transducer (CMUT). An electro-capacitive pressure sensor, such as a CMUT, may respond to an applied electrical stimulus to provide a mechanical resonance. This resonance may provide a measurable frequency response. Through calibration, a frequency response may provide a measurable "static" pressure response. Sequential temporal samples may be indicative of "dynamic" pressure. An electro-capacitive pressure sensor may be substantially free of lead and/or offer high sensitivity.

The at least one pressure sensor may comprise material that embeds one or more micro-electromechanical system (MEMS) devices. MEMS devices may include piezoelectric transducer components. MEMS devices may include capacitive micro-machined ultrasonic transducer (CMUT) components.

The pressure sensor may have a low Q-factor. A low Q-factor provides a broad bandwidth of resonance.

Where a plurality of pressure sensors is deployed, each of the pressure sensors may detect a small part of the whole bandwidth of interest. For example, each of the pressure sensors in the plurality of pressure sensors may detect a discrete frequency band. Each pressure sensor may have a high Q-factor giving selectivity. The pressure sensor that provides the measurable response with the highest amplitude of vibration may be indicative of the pressure differential between the exterior of the tube and the internal bore.

A single pressure sensor may embed one or more MEMS devices that incorporate a plurality of internal sensors together with a selection processing capability. The pressure sensor may be made from a ceramic material. The pressure sensor may be lead-containing. The piezoelectric pressure sensor may comprise lead zirconate titanate. The piezoelectric pressure sensor may be lead-free. The piezoelectric pressure sensor may comprise one or more of barium titanate, bismuth sodium titanate, bismuth potassium titanate, sodium niobate, potassium niobate, potassium sodium niobate, and poly(vinylidene difluoride) (PVDF).

The stimulus may be an electrical stimulus. The pressure sensor may be configured to receive an electrical stimulus. The electrical stimulus may be an AC voltage. The electrical stimulus may be pulsed. The electrical stimulus may have any waveform. The electrical stimulus may impart resonance in a part of the pressure sensor.

The pressure sensor may be electrically isolated from the tube. Keeping the pressure sensor isolated from the tube allows electrical stimulation of the pressure sensor without stimulating the tube.

The externally facing region of the pressure sensor may comprise a coating. A coating isolates the pressure sensor from the body when inserted therein. The externally facing region may comprise an electrically insulating coating. An electrically insulating coating may isolate the current in the pressure sensor from the body (or body tissue) when inserted therein. The externally facing region may comprise a biocompatible coating. A biocompatible coating may enable the device to be inserted into body tissue for extended periods of time. This may be beneficial for pressure measurements over an extended period of time. The coating may be a polymer. The coating may be poly(p-xylylene).

The measurable response may be an electrical response. The measurable response may be an ultrasound response. The measurable response may be indicative of an electrical impedance of the pressure sensor. The electrical impedance of the pressure sensor may vary with the pressure differential between the exterior of the tube and the internal bore.

The measurable response may be an amplitude, such as an amplitude of vibration. The measurable response may be a resonant amplitude. The measurable response may be indicative of an amplitude, such as an amplitude of vibration. The measurable response may be indicative of a resonant amplitude.

The measurable response may be indicative of a resonant frequency of the pressure sensor. The resonant frequency of the pressure sensor may vary with the pressure differential between the exterior of the tube and the internal bore. That is, the resonant frequency may correlate to the pressure differential. The resonant frequency may be a transverse mode of the pressure sensor. The resonant frequency may be a thickness mode of the pressure sensor. It will be appreciated that other vibrational modes are possible. The resonant frequency may be a composite of several vibration modes. Using the resonant frequency as an indication of the pressure differential can provide improved sensitivity of the device. The resonant frequency may be dependent on at least the length, width, thickness and material of the pressure sensor. The pressure sensor may have a resonant frequency between 0.1 MHz and 100 MHz. The resonant frequency may be between 1 MHz and 20 MHz. The resonant frequency may be between 1 MHz and 7 MHz. The resonant frequency may be between 7 MHz and 16 MHz. The resonant frequency may be between 16 MHz and 22 MHz. The resonant frequency may be between 1 MHz and 4 MHz. The resonant frequency of the pressure sensor may be between 0.1 MHz and 5 MHz, between 5 MHz and 20 MHz, between 20 MHz and 40 MHz, between 40 MHz and 60 MHz, between 60 MHz and 80 MHz, or between 80 MHz and 100 MHz. The resonant frequency may be between any combination of upper and lower limits provided above. The resonant frequency may be determined based on the desired use of the device.

The measurable response may be indicative of a capacitance of the pressure sensor. The measurable response may be indicative of a change in capacitance of the pressure sensor.

The measurable response may be indicative of a change in pressure differential between the exterior of the tube and the internal bore.

The measurable response may be indicative of a change in electrical impedance of the pressure sensor.

The tube may further comprise a non-insertion portion. The opening may be located at the non-insertion portion.

The device may further comprise a user-holdable portion (or handle) which is in connection with the tube. The user-holdable portion may be in connection with the non-insertion portion. The user-holdable portion may house electrical components, such as the processor. The user-holdable portion may comprise a display for displaying the measured pressure differential.

The internal bore may be in communication with ambient pressure via the user-holdable portion.

The user-holdable portion may comprise one or more of a hand-grip, a finger-grip, and/or a thumb-grip. The hand-grip, finger-grip, and thumb-grip may help a user to operate the device. The device may be a handheld device. The device may be a portable device.

The user-holdable portion may comprise a tube or needle penetration depth indicator for indicating a tube or needle penetration depth into the body. The tube or needle penetration depth indicator may assist a user to insert the tube or needle to a desired tube or needle penetration depth. The tube or needle penetration depth indicator may allow the user to re-insert the tube or needle to the same depth repetitiously if multiple pressure measurements are required. Recording the pressure measurements at the same depth helps to reduce experimental variances in repeated pressure measurements. The penetration depth indicator may comprise a measurement scale. The penetration depth indicator may comprise a pointer indicating the tube or needle penetration depth.

The tube or needle penetration depth indicator may comprise one or more legs relatively moveable with respect to the tube or needle. The legs may be relatively moveable with respect to the user-holdable portion. The legs may slide in relative to the tube or needle upon insertion of the tube or needle into a body. The legs may comprise the measurement scale.

The user-holdable portion may comprise a penetration restraint mechanism configured to limit the tube or needle penetration depth. It may be beneficial to limit the tube or needle penetration depth to prevent inserting the tube or needle too deep into the body. The penetration restraint mechanism may comprise a locking means, such as a friction clip. The locking means may clamp the legs of the penetration depth indicator, thereby preventing relative movement of the legs with respect to the user-holdable portion. Other locking means to restrict the movement of the legs with respect to the user-holdable portion may be contemplated. The locking means can retain the tube or needle at a stable injection depth. This is advantageous if the patient is required to move during pressure measurement.

The user-holdable portion may comprise a fastening member for fastening the device to the body. The fastening member may allow the device to remain secure, stable and stationary when inserted into a body for an extended period of time. Using the fastening member to securely fasten the device to the body enables pressure measurements to be recorded whilst the body is moving, for example, during activity or clinical tests. The fastening member may facilitate the measurement of exertional compartment pressure. The fastening member may comprise one or more flanges. The flanges may be wing-tabs. The fastening member may be fastened to the body using an adhesive tape. The fastening member may comprise a belt or strap.

The device comprises a processor configured to correlate the measurable response with the pressure differential between the exterior of the tube and the internal bore. The processor may use a calibration curve to correlate the measurable response with said pressure differential. The processor may be operable to provide a stimulus to the pressure sensor. The processor may be electrically connected to the pressure sensor via wires disposed in the internal bore. The wires may be disposed outside of the internal bore. The wires may be electrically insulated from the tube. The wires may have a length of less than 500 mm. The wires may have a length of less than 200 mm. The wires may have a length of less than 100 mm. Wires with a shorter length may provide improved electrical impedance measurements due to their lower reactive electrical load.

The processor may be electrically connected to the pressure sensor via a wireless connection.

The processor may be housed within the user-holdable portion.

The processor may be housed within a central processing unit. The central processing unit may process the measureable responses from one or more devices.

The tube may be a needle. The tube may have a cross-sectional diameter of between 0.1 mm and 5 mm. The tube may have a cross-sectional diameter of between 0.5 mm and 2.1 mm.

The tube may have a length of between 10 mm and 150 mm. The tube may have a length of between 50 mm and 80 mm.

The pressure sensor may have a cross-sectional dimension between 0.1 mm and 25 mm. The pressure sensor may have a cross-sectional dimension of between 0.2 mm and 10 mm. The pressure sensor may have a cross-sectional dimension of between 1 mm and 5 mm. The externally facing region may have a cross-sectional dimension of between 1 mm and 3 mm. These cross-sectional dimensions may be a cross-sectional length or a cross-sectional width.

The pressure sensor may have a thickness of less than 1 mm. The pressure sensor may have a thickness of less than 0.5 mm. The pressure sensor may have a thickness of less than 0.27 mm. The thickness of the pressure sensor may be defined as the distance between the internally facing region and the externally facing region.

According to a second aspect of the invention there is a kit of parts comprising: the device according to any previous claim; and an insertion site guide for indicating a tube insertion site.

The insertion site guide may comprise a wearable sleeve or sheet. The insertion site guide may indicate the position of muscular compartments. This may allow a user of the device to insert the device into the same location repetitiously. This is particularly beneficial for identifying the correct compartment location, and for reliably inserting the tube or needle into the same location if multiple tube or needle insertions are required.

According to a third aspect of the invention there is a method of measuring a pressure differential using the device according to the first aspect, the method comprising the steps of:

providing a stimulus to the pressure sensor so that the pressure sensor provides a measurable response;

measuring the measurable response, wherein the measurable response is indicative of the pressure differential between the exterior of the tube and the internal bore, the internal bore being in communication with ambient pressure via the opening in the tube; and correlating the measurable response with the pressure differential between the exterior of the tube and the internal bore.

The pressure differential may be a change in pressure differential.

The stimulus may be an electrical stimulus. Providing a stimulus, such as an electrical stimulus, to the pressure sensor can improve the sensitivity of the device. This allows the pressure sensor to be miniaturised whilst maintaining acceptable levels of sensitivity.

The method may further comprise the step of calibrating the device. The step of calibrating the device may comprise the sub-steps of:

providing a stimulus to the pressure sensor whilst maintaining the externally facing region of the pressure sensor at ambient pressure so that the pressure sensor provides a measurable calibration response indicative of the pressure differential between the exterior of the tube and the internal bore;

measuring the measurable calibration response; and correlating the measured calibration response with a pressure differential of zero.

The stimulus used in the calibration step may be an electrical stimulus. The calibration step uses ambient pressure as a reference pressure. The ambient pressure may be atmospheric pressure. This eliminates the necessity to use balanced syringes, manometer lines and the like to calibrate the device. The device may self-calibrate. That is, a change in the ambient pressure will affect the pressure within the internal bore and the pressure within a body (when inserted therein) to the same extent. Therefore, the pressure differential is unaffected and drifts in pressure measurement are avoided.

The method may further comprise the step of applying an electrical stimulus to the pressure sensor. The step of measuring the measurable response may be performed at least partially during the step of applying the electrical stimulus to the pressure sensor.

The stimulus may be an alternating electrical stimulus, such as an AC voltage. The stimulus may be a pulsed electrical stimulus. The stimulus may be an ultrasound stimulus. The stimulus may cause the pressure sensor to vibrate. The stimulus may cause the pressure sensor to resonate at a resonant frequency.

The frequency of the stimulus may be varied. The frequency of the stimulus (e.g. electrical stimulus) may be increased or decreased from a first frequency to a second frequency, for example, as a frequency sweep. The frequency of the stimulus may be constant. The stimulus may comprise a frequency that is substantially the same as the resonant frequency of the pressure sensor. The stimulus may have a frequency between 0.1 MHz and 100 MHz. The stimulus may have a frequency of between 1 MHz and 7 MHz. The stimulus may have a frequency of between 1 MHz and 4 MHz. The stimulus may have a frequency of between 16 MHz and 22 MHz. The frequency of the stimulus may be between 0.1 MHz and 20 MHz, 20 MHz and 40 MHz, between 40 MHz and 60 MHz, between 60 MHz and 80 MHz, or between 80 MHz and 100 MHz. The frequency of the stimulus may be between any combination of upper and lower limits provided above. The first and second frequencies may be any combination of the upper and lower limits provided above.

The frequency (or range of frequencies) of the stimulus may be dependent upon the previously measured pressure differential. The frequency of the stimulus may be varied in a localised range comprising a frequency that correlates to the pressure differential of the previous measurement. For example, the frequency of the stimulus may be varied in a localised range comprising a frequency that provided the maximum resonance of the previous measurement. The localised range may be about ±5 Hz, ±2 MHz, ±1 MHz, or ±0.5 MHz of the frequency that correlated to the pressure differential of the previous measurement. The frequency of the stimulus may start at the frequency that correlated to the pressure differential of the previous measurement and step outwardly (i.e. higher and lower) therefrom until the current pressure differential is determined, for example, until a new maximum resonance value is measured. Using a localised range of stimulus frequencies can help reduce power consumption of the device and can extend battery life.

The measurable response may be an ultrasound response.

The measurable response may be an electrical response.

The measurable response may be indicative of an electrical impedance of the pressure sensor.

The measurable response may be indicative of a resonant frequency of the pressure sensor.

The measurable response may be indicative of a change in electrical impedance of the pressure sensor.

The method may further comprise the steps of:

removing the stimulus from the pressure sensor;

measuring the measurable response, wherein the measurable response is indicative of a change in pressure differential between the exterior of the tube and the internal bore; and correlating the measurable response with the change in pressure differential.

The steps of providing the stimulus and removing the stimulus may be alternated repeatedly whilst measuring the measurable response. This can enable both static and dynamic pressures to be measured with a reduced power consumption.

The measurable response may be measured at a sampling rate of between 6 samples per hour and 25 samples per second. The sampling rate may be between 1 sample per minute and 10 samples per second. The sampling rate may be at least 10 times faster than the arterial pulse rate.

The pressure differential between the exterior of the tube and the internal bore may be between −200 mmHg and +200 mmHg. The pressure differential may be between −120 mmHg and +120 mmHg. The pressure differential may be between 0 mmHg and +60 mmHg.

The pressure exterior to the tube may be a compartment pressure, spinal cord pressure, intracranial pressure, interstitial pressure, arterial pressure, venous pressure, and/or atmospheric pressure. The body may have a body pressure that is isolated from ambient pressure. The body may be a pressurised chamber, such as a tyre, a sealed chamber, such as a sealed reaction vessel, or a low pressure chamber, such as a vacuum chamber.

Whilst the invention has been described above, it extends to any inventive combination of the features set out above or in the following description, drawings or claims. For example, any feature described in relation with the first aspect of the invention is considered to be disclosed also in relation to the second and third aspects of the invention.

BRIEF DESCRIPTION OF THE DRAWINGS

Embodiments of the invention will now be described, by way of example only, with reference to the accompanying drawings, in which.

DETAILED DESCRIPTION

Figures 1, 2:
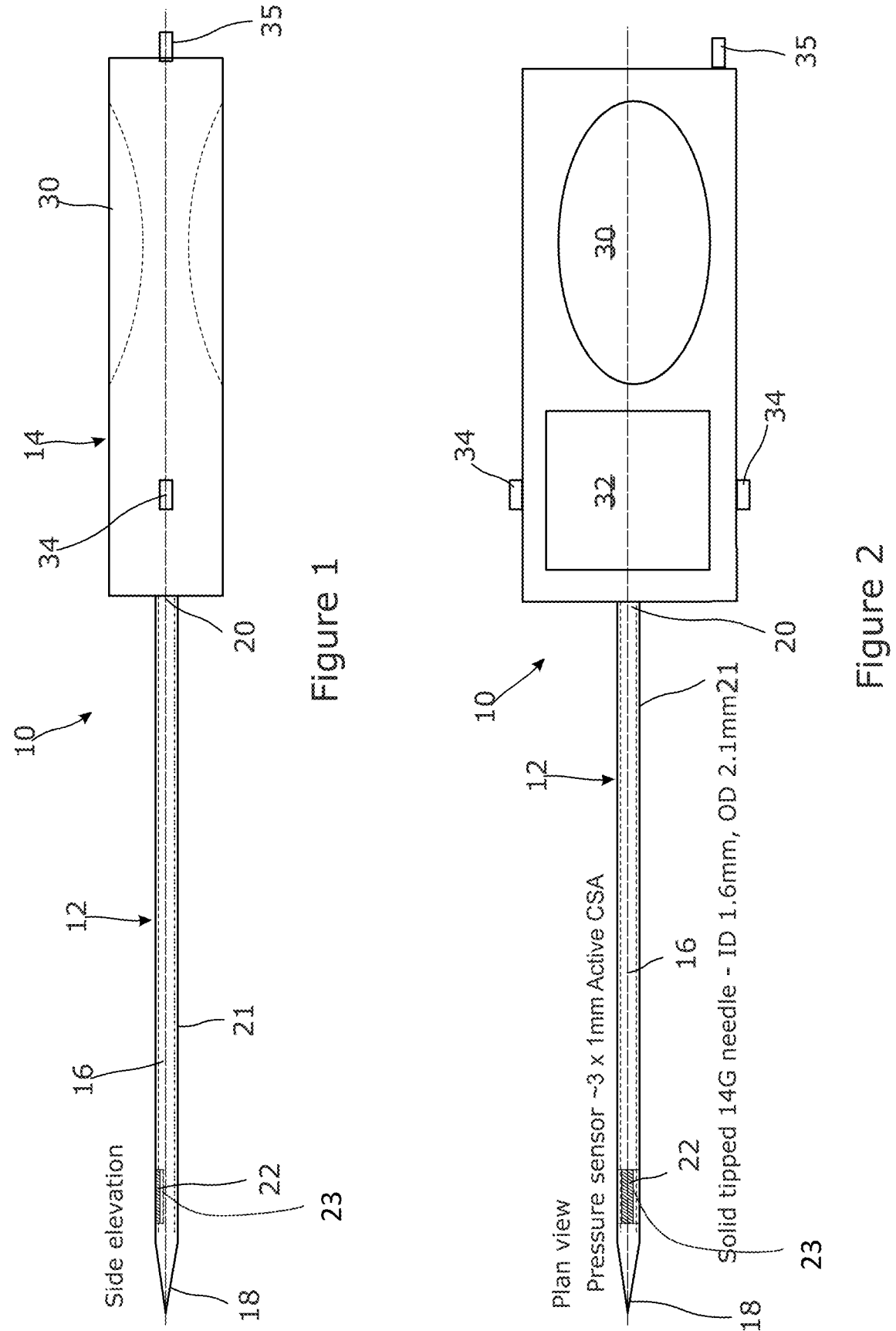
FIG. 1 is a schematic side view of a device according to a first embodiment of the invention.
FIG. 2 is a schematic plan view of a device according to a first embodiment of the invention.
Figure 2A:
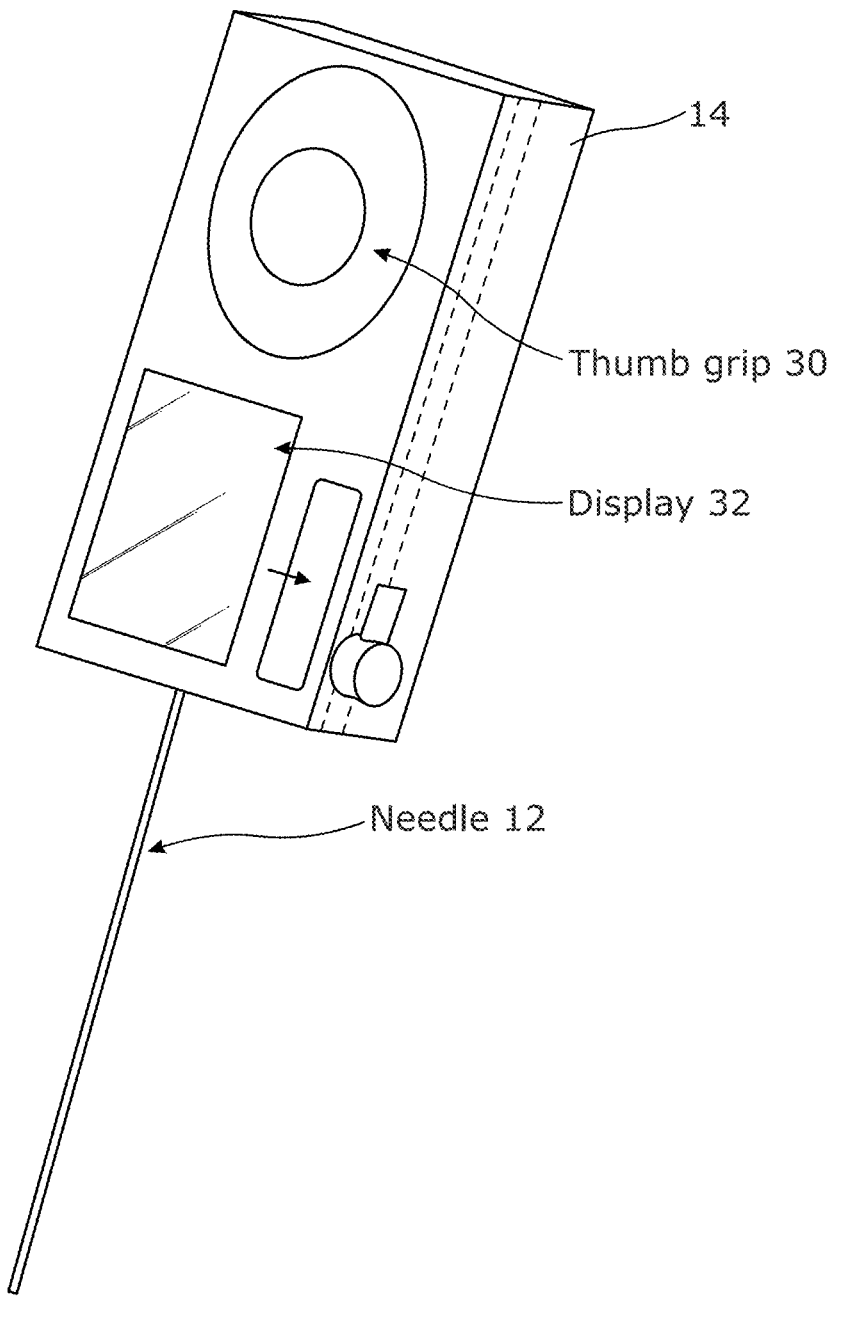
FIG. 2A is a perspective view of the device according to a first embodiment of the invention.

FIGS. 1, 2 and 2A illustrate a device (shown generally at 10) for measuring a pressure differential in a body according to a first embodiment of the invention. The device 10 comprises a tube 12 and a handgrip (or handle) 14. The tube 12 is hollow, comprising an internal bore 16, a tube wall 17, a closed first end (or tip) 18, and an open second end 20. The bore 16 is delimited by walls 21 and the closed first end 18. In the first embodiment the tube 12 is a needle. The closed first end 18 is sharp to allow the needle 12 to be inserted into a patient body by penetrating body tissue. In other embodiments, the closed first end is blunt. The internal bore 16 is maintained at ambient atmospheric pressure. In the first embodiment, the open second end 20 is in open communication with the atmosphere, and therefore the internal bore 16 maintained at ambient atmospheric pressure. The second end 20 of the needle 12 extends into the handgrip 14. In some embodiments, the handgrip 14 comprises breather holes (or slits) 35 to allow the open end 20 to be exposed to the atmosphere. The breather holes 35 ensure that the internal bore 16 remains in communication with atmospheric pressure. In the first embodiment, the internal pressure ($P_{bore}$) in the bore 16 is maintained at atmospheric pressure due to the open second end 20. The pressure in the bore 16 of the needle 12 is used as a known reference pressure.

Figures 3A, 3B, 4:
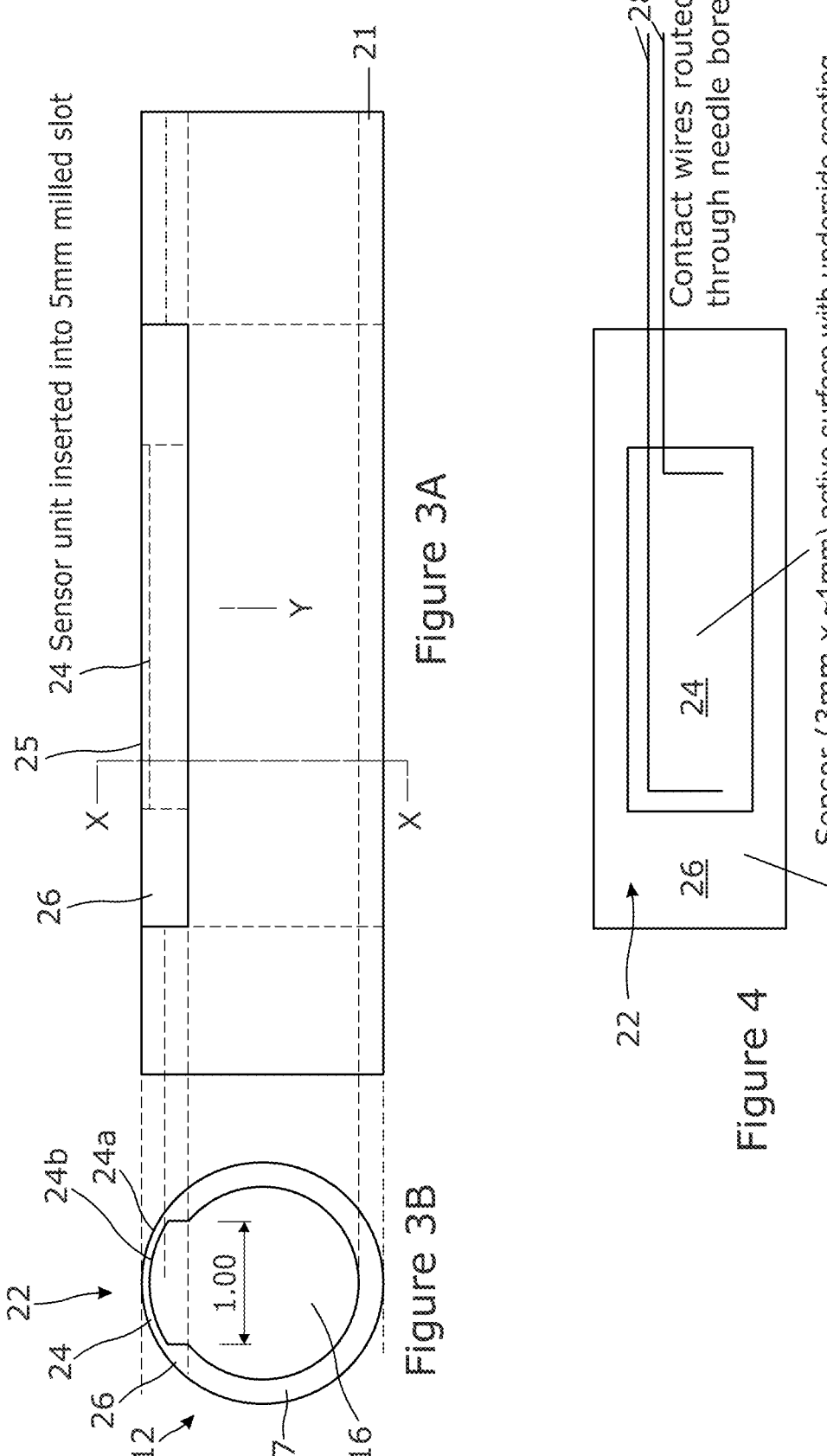
FIG. 3A is a schematic side view of the sensor.
FIG. 3B is a schematic cross-sectional view of the needle/tube at the line X-X.
FIG. 4 is a schematic underside view at the line Y.

The needle 12 further comprises a pressure sensor 22, shown in more detail in FIGS. 3A, 3B and 4. The sensor 22 is set into a slot or other aperture 23 formed in the walls 21 of the needle 12. In some embodiments, the needle 12 comprises a plurality (or array) of discrete pressure sensors set into a single slot. In other embodiments, the needle 12 comprises a plurality of slots with one or more sensors set into each slot. In some embodiments, there is a plurality of sensors arranged along the needle length (e.g. in a "ladder" arrangement), each sensor providing a discrete sensing element. In some embodiments each sensor is optimised to detect a specific pressure range.

The slot 23 is conveniently formed using known machining (or electro-machining) methods. The sensor 22 is shaped to be substantially flush with the walls 21 so as not to obstruct or impede the movement of the needle during insertion. That is, the walls and sensor provide a substantially smooth outer surface during needle insertion. In the first embodiment, the sensor 22 is a sector of a hollow cylinder in shape. The sector may be up to a maximum of a hemi-cylinder in some embodiments. Other two- or three-dimensional geometries of the sensor, such as square, rectangular, ellipse, circular, oval, or annular may be employed in other embodiments. In some embodiments, the sensor has a geometry optimised to detect specific forcing modes, for example a "hoop" stress component. In other embodiments, the sensor has a longitudinal component to detect a pressure pulse passing along a vessel.

The sensor 22 comprises an active surface 24 and a non-active surface 26. The sensor has an externally facing region and an inwardly facing region. The active surface 24 of the sensor 22 comprises an externally facing active surface 24a and an internally facing active surface 24b. The externally facing active surface 24a faces outwardly, and is in communication with a pressure exterior to the bore 16 of the needle 12. That is, the externally facing active surface 24a is in communication with an external load pressure (P$_{ext}$). When the needle 12 is inserted into a body, the external active surface 24a is in communication with the body interior (e.g. body tissue). When the needle 12 is inserted into a body, the external pressure corresponds to the pressure in the body interior. The body pressure may be a compartment pressure. In some embodiments, the external active surface 24a comprises a coating 25. The coating 25 physically isolates the active surface 24 from the body, for example, isolating the chemical components of the sensor from the body interior. This is of particular benefit if the sensor 22 comprises a potentially harmful chemical, such as a lead-containing material. In some embodiments, the coating 25 (or an additional coating layer) electrically isolates the active surface 24 from the body. In some embodiments, the coating is a polymer coating. In some embodiments, the polymer is poly(p-xylylene).

The internally facing active surface 24b faces inwardly, and is in communication with the internal pressure (P$_{bore}$) within the bore 16. A pressure differential (P$_{ext}$–P$_{bore}$) exists between the external pressure (P$_{ext}$) and the internal pressure in the bore 16. The principle sensing action of the pressure sensor (P$_{bore}$) arises due to flexure in the pressure sensor as the pressure differential (P$_{ext}$–P$_{bore}$) varies. This flexure can provide a measurable response to be generated.

The non-active surface 26 is attached to the walls 21 of the needle 12. In the first embodiment, a non-conductive adhesive is used. The active surface 24 and the walls 21 are electrically isolated.

In some embodiments, the active surface 24 of the sensor 22 comprises an electro-mechanical material or material that embeds one or more micro-electromechanical system (MEMS) devices. In the first embodiment, the active surface 24 comprises a piezoelectric material or transducer. In some embodiments, the piezoelectrical material has a low Q-factor. In other embodiments, for example, where a plurality of sensors is deployed each sensor may have a high Q-factor.

In some embodiments, the sensor 22 comprises a ceramic. In some embodiments the piezoelectric material is an inter-metallic inorganic polycrystalline ceramic compound. In some embodiments the piezoelectric material is lead-containing, such as lead zirconate titanate. In other embodiments, the piezoelectric material does not containing lead, and, for example, may be formed from barium titanate, bismuth sodium titanate, bismuth potassium titanate, sodium niobate, potassium niobate, and/or potassium sodium niobate. In further embodiments, the sensor 22 comprises poly(vinylidene difluoride) (PVDF). PVDF exhibits long-term biocompatibility.

A piezoelectric material produces an electrical signal in response to a change in external physical or mechanical stimulus. The electrical signal may be an electro-motive force (or a voltage) which changes in response to a change in the external stimulus, such as a change in applied mechanical force. The external stimulus may, for example, be an applied stress caused from a change in pressure differential across the sensor. A change in applied stress may cause the impedance of the piezoelectric material to change.

However, the measurable change in voltage (or impedance) will decay very rapidly if the change in external physical or mechanical stimulus ceases.

A piezoelectric sensor also responds to an applied electrical stimulus. For example, an applied electrical stimulus (of appropriate frequency) may cause a piezoelectric sensor to resonate at a characteristic resonant frequency. The resonant frequency is dependent upon the pressure differential across the sensor. The resonant frequency may be determined using known processing techniques.

In some embodiments, it is preferable for the sensor 22 to be formed from a piezoelectric material that has a narrow resonant peak (i.e. a high Q factor). This helps to improve the sensitivity of the device 10. That is, a change in pressure differential can be detected as a well-defined change in resonant frequency. In other embodiments, a low Q-factor is used to give a broad range of resonant frequency with good sensitivity. It may be preferable to use a Q-factor having an intermediate value. This compromise provides a broad based of resonance, whilst giving a higher resonance response.

The impedance of a piezoelectric sensor is also dependent upon the pressure differential. Measuring the electrical impedance at a particular frequency may be correlated with a pressure differential across the sensor.

Contact wires 28 form an electrical contact between the sensor 22 and processor located in the handgrip 14. In the first embodiment, the processor correlates electrical signals (or responses) from the sensor 22 with a pressure differential (P$_{ext}$–P$_{bore}$). In the first embodiment, the contact wires 28 are disposed within the bore 16. However, in other embodiments, the contact wires are disposed on the outside of the bore. The contact wires 28 are electrically isolated from the walls 21.

The contact wires 28 relay electrical signals between the processor (not shown) and the sensor 22. For example, the contact wires 28 allow electrical power or an electrical stimulus (including electrical pulses or other waveforms) to be applied to the sensor 22. The contact wires 28 also allow electrical signals generated by the sensor 22 to be measured by the processor.

In other embodiments, the processor is disposed within the bore 16. The invention is not limited by location of the processor. In some embodiments the processor provides one or more of signal amplification, signal conditioning, and/or analogue to digital encoding. In some embodiments the processor is wirelessly connected to the sensor 22. In further embodiments, the processor is disposed in a central processing unit, suitable for data storage and data analysis of one or more devices 10. For example, the central processing unit may be configured to store a timed sequence of regular measurements to track trends in pressure over time. The central processing unit may provide power, enable control of the device 10, and display pressure readings. In some embodiments, the processor provides an alert if the measured pressure, such as a compartment pressure or intracranial pressure, exceeds a pre-determined threshold value set by the user. In some embodiments, the central processing unit is configured for bidirectional communication with the pressure sensor. The central processing unit may provide additional facilities for comparative display of a plurality of pressure values obtained from a plurality of pressure measurements. The display may show raw or processed data. The central processing unit may comprise a user interface which provides individual control to one or more devices connected to the central processing unit. Conveniently, the central processing unit may be configured to be a fixed installation, for example at a bedside.

Figure 5:
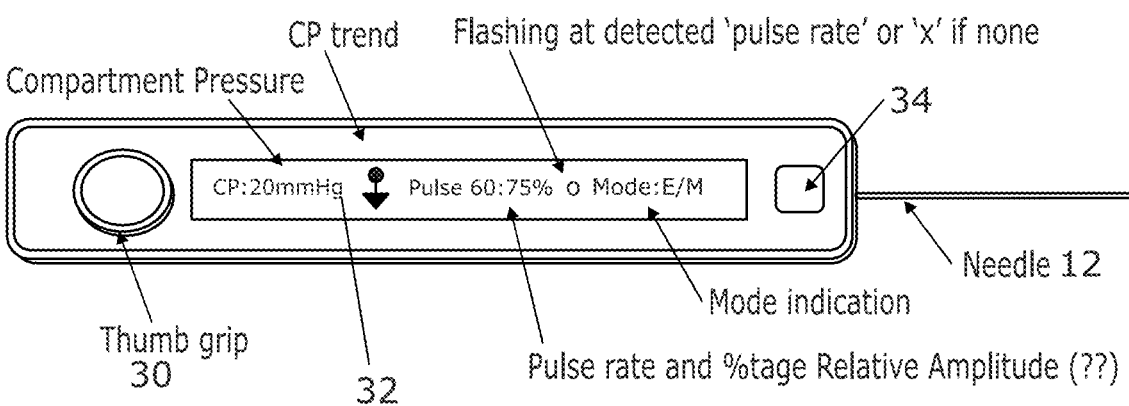
FIG. 5 is a perspective view of a device of the first embodiment.

The handgrip 14 may further comprise a thumb grip 30, a display 32, and measurement controls 34 (FIG. 5), and a breather hole, or slit, 35 to equalise atmospheric pressure within the body of the device. The thumb grip 30 provides additional support and comfort to the user. Embodiments comprising a handgrip 14 may be portable devices. The display 32 provides a read-out of the measured pressure differential and other parameters, which may be measured simultaneously, such as arterial pulse rate. In some embodiments the display includes an alert system dependent upon the measured pressure differential. In some embodiments the display flashes to indicate the pulse rate. The measurement controls 34 allow the user to initiate the device, zero the device, and/or operate the device in the desired mode, for example, providing a switch between stimulated and passive operational modes as described below. In some embodiments, the measurement controls 34 allow the sampling rate to be adjusted by the user.

Figure 6:
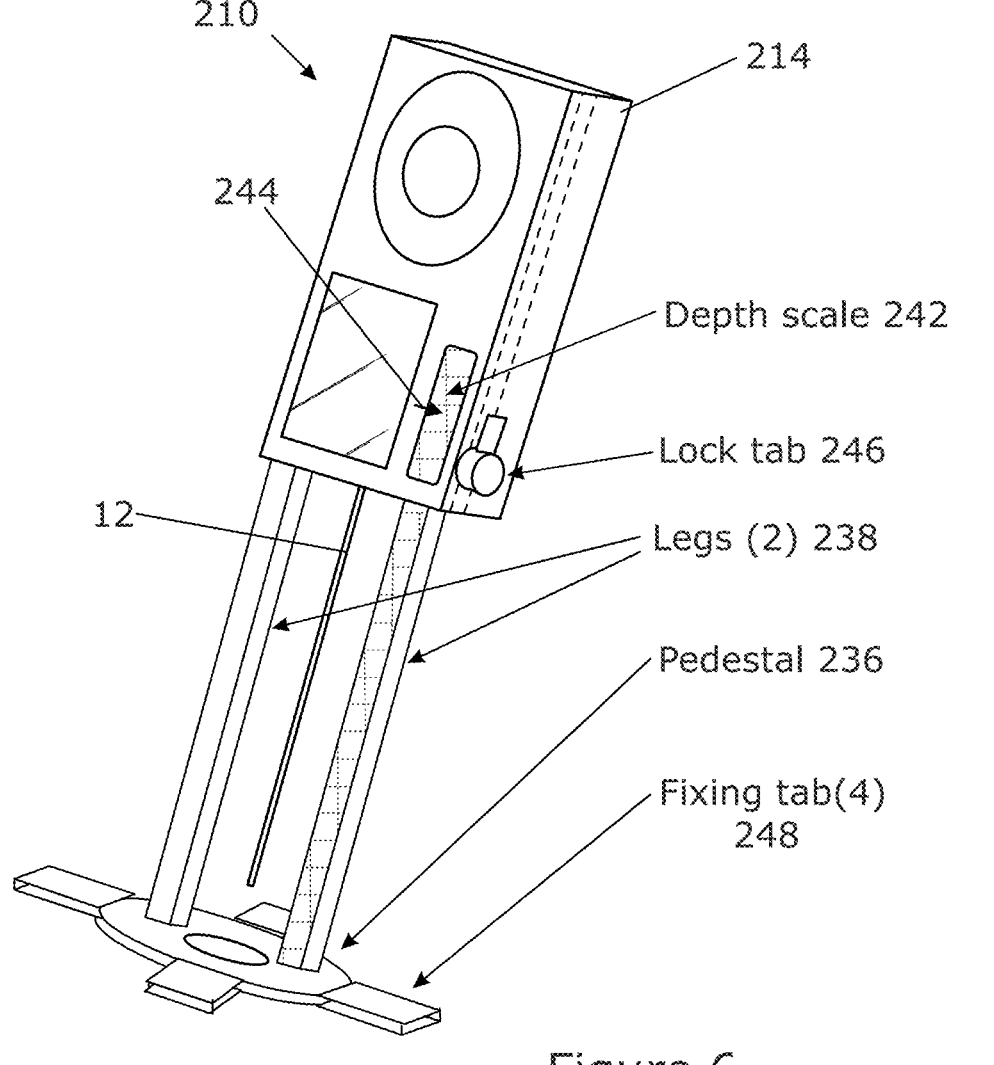
FIG. 6 is a perspective view of a second embodiment of the invention.

In a second embodiment, the device 210 (shown in FIG. 6) further comprises a means for indicating and controlling the needle penetration depth on insertion into a body. The same reference numerals as used in previous Figures have been used in FIG. 6 to refer to features that are identical. The second embodiment is formed in a similar manner to the first embodiment. However, the handgrip 214 further comprises a pedestal 236. The pedestal 236 is a substantially circular band, having the needle 12 disposed at its centre. The diameter of the pedestal 236 is optionally the same width as the handgrip 214. The invention is not limited by the geometry of the pedestal 236. The pedestal 236 further comprises legs 238 configured to slide in complementary grooves in the handgrip 214 when the needle 12 is inserted into a body. The legs 238 comprise a scale 242 and a pointer 244. When the needle is inserted into a body, the movement of the legs 242 in the grooves allows the depth of the penetration to be determined using the scale 242 and pointer 244. This configuration beneficially provides a precise indication of needle penetration and allows a user, such as a clinician, to repeatedly insert the needle 12 to the same desired depth for long-term or repeated pressure measurements.

The handgrip 214 further comprises a locking means, such as a friction clip or lock tab 246, to restrain the movement of the legs, thereby securing the legs 238 at a fixed, desired position. This beneficially prevents unwanted further movement or penetration of the needle when the required depth is attained. That is, the friction clip 246 limits the needle penetration depth into a body.

The device 210 further comprises a fixation means or an anchor 248 in the form of wing-tabs. The anchor 248 provides a surface allowing the device 214 to be fixed or attached to the body, for example, by adhesive tape or a strap.

In operation, the device 10 is first initiated by supplying a power supply to the processor whilst the device is outside of a patient body. The power supply provides an electrical source to electronic components in the device, such as the sensor 22 and the processor. The supplied power enables pressure measurement, data processing and display.

In the first embodiment, a pull-tab initially prevents contact between the power supply and the processor so that the electrical circuit is incomplete. The device 10 is initiated by closing an electrical contact between the power supply and the processor, thereby completing the electrical circuit. In the first embodiment, the device is initiated by removing the pull-tab to complete the electrical circuit. In another embodiment, the electrical contact is formed on removal of a suitable needle shield or sheath. Removal of the needle shield completes the electrical circuit and initialises the device. This beneficially necessitates that the device is initiated, and calibrated, prior to insertion into a body. Other embodiments employ other known methods of completing the electrical circuit, such as connecting an external power source, using a mechanical switch, button, or other known method of supplying power to electrical circuitry.

Devices 10, 210 used in medical applications may be single-use devices to avoid contamination and to reduce the risk and spread of infection. In single-use devices, the power may be supplied by a battery, which continuously supplies power until the battery is fully discharged. A pull-tab initialisation mechanism provides a one-time initiation method so that the battery may continuously supply power to the electrical circuitry until the battery has fully discharged. This is particularly beneficial for disposable or single-use devices, and helps to prevent re-use, which could lead to an increased risk of infection.

Some embodiments of the device may be used multiple times, with sterilisation techniques used between each use. It is beneficial for a multiple use device to have power switches and/or replaceable/rechargeable batteries to conserve battery power when not in use.

When the device is initiated, an auto-calibration (or self-calibration) step is performed, as detailed below. When the device of the first or second embodiment of the invention is initiated outside of a body, the external pressure ($P_{ext}$) and the internal bore pressure ($P_{bore}$) are both at atmospheric pressure. That is, the pressure differential ($P_{ext}-P_{bore}$) is 0. Therefore, there is no net external strain on the sensor. The bore, processor uses this initial condition (i.e. $P_{ext}=P_{bore}$) to determine a zero relative pressure state, thereby self-calibrating the device 10. This initial condition sets a calibration baseline. The device measures changes in pressure differential based on this calibrated baseline.

When the needle 12 is inserted into a body, the inner bore 16 remains in direct contact with atmospheric pressure. Therefore, the internal pressure ($P_{bore}$) maintains at ambient atmospheric pressure. The internal bore pressure ($P_{bore}$) is used as a known reference pressure value.

However, upon insertion into a body, the exterior of the needle 12 is subjected to a change in external pressure ($P_{ext}$). The external pressure is representative of the pressure within the body. For example, if the needle is inserted into a muscular compartment, the external pressure acting on the needle would correspond to the compartment pressure. When the needle 12 is fully inserted into a body, the internal bore pressure ($P_{bore}$) is isolated from the external pressure ($P_{ext}$) by the sealed walls 21, closed end 18, and sensor 22. It is preferable for the walls 21 to have a degree of rigidity to withstand the changes in external pressure ($P_{ext}$), so that the bore 16 is not deformed upon insertion.

Due to the constant internal pressure ($P_{bore}$) within the bore 16, but change in external pressure ($P_{ext}$), a change in pressure differential ($P_{ext}-P_{bore}$) is observed. Consequently, the forces acting on the sensor are unbalanced (or asymmetrical). The pressure differential ($P_{ext}-P_{bore}$) or change in pressure differential ($\Delta(P_{ext}-P_{bore})$) is correlated to a change in electrical and/or mechanical properties of the sensor 22, which provide a measurable response.

In some embodiments, the pressure differential ($P_{ext}-P_{bore}$) is correlated to the electrical impedance of the sensor 22. In other embodiments, the pressure differential ($P_{ext}-P_{bore}$) is correlated to the resonant frequency of the sensor 22. In further embodiments, the change in pressure differential ($\Delta(P_{ext}-P_{bore})$) is correlated to an electrical property of the sensor (e.g. impedance) or a signal generated by the sensor. In some embodiments, the processor is configurable to simultaneously or selectively measure one or more of the electrical impedance, the resonant frequency and/or electrical signals generated from the sensor 22. Consequently, the pressure differential ($P_{ext}$–$P_{bore}$) or change in pressure differential can be measured.

The processor is configured to correlate one or more of a measured electrical impedance, resonant frequency, and/or signal generated by the sensor 22 with the external pressure ($P_{ext}$). This may, for example, be carried out using calibration curves based on the auto-calibration step.

By using intrinsic properties of the material to determine the pressure differential ($P_{ext}$–$P_{bore}$) there is no need to use balanced hydraulics, or manometer lines for the pressure measurement. Further, variations in temperature have negligible effects on the accuracy of the pressure measurement. Ambient pressure changes affect both the internal pressure in the bore 16 ($P_{bore}$) and pressure in the body equally, and therefore do not affect pressure measurements. Moreover, long-term drift in pressure measurements is negligible since the reference pressure is atmospheric pressure.

The auto-calibration step does not rely on removal of air bubbles from a syringe or on manometer lines. Further, the reference pressure ($P_{bore}$) inside the bore 16 remains at a fixed pressure when the device is orientated at any angle. Therefore, it is not necessary to perform the calibration step at the same angle as the pressure measurement, which allows more reliable pressure measurements to be taken. For these reasons the device 10, 210 provides a simplified calibration process compared to known pressure sensors, and allows accurate and reliable pressure measurements to be taken whilst a patient is moving or active, for example, in the measurement of exertional compartment pressure.

A clinician may be interested in at least some of the following parameters:

a. instantaneous compartment pressure (relative to atmospheric pressure);

b. trends or variations of the compartment pressure over an extended period;

c. fractional (percentage) over-pressure variation from detected pulsatile arterial blood flow (also known as delta pressure);

d. arterial pulse rate; and e. intracranial pressure, particularly following surgery.

One or more of these, or other, clinically useful parameters may be measured using embodiments of the invention by adopting a variety of exemplary methods or modes. For example, embodiments of the present invention can be used to measure static and/or dynamic pressures.

In a first exemplary method (or first exemplary stimulated mode), the device 10, 210 allows an instantaneous (or static) pressure, such as an instantaneous compartment pressure, to be measured. The first exemplary method is also suitable for measuring trends in compartment pressure over extended periods. Dynamic pressures can also be measured. A second exemplary method (described below) is further suitable for determining pulse rates, and amplitudes of the cardiac variation.

On initialisation, the processor applies a stimulus, such as an electrical or ultrasound stimulus, to the sensor 22. The electrical stimulus is applied at a known, pre-determined frequency and causes the sensor 22 to vibrate. In some exemplary methods, the electrical stimulus is an AC voltage. However, pulsed stimuli or other waveforms are applied in other exemplary methods. At a characteristic frequency, the sensor 22 will resonate at a resonant frequency.

The electrical impedance of the sensor is measured using known processing techniques. The electrical impedance of the sensor is indicative of (and dependent upon) the pressure differential ($P_{ext}$–$P_{bore}$). Therefore, it is possible to correlate the change in electrical impedance to the pressure differential ($P_{ext}$–$P_{bore}$) or external load pressure ($P_{ext}$), for example, by using a calibration curve.

The maximum sensitivity of the impedance measurement occurs when measured at a specific advantageous frequency. In some exemplary methods, this advantageous frequency corresponds to the resonant frequency of the sensor.

In some exemplary methods, the measured electrical impedance is indicative of a mean static pressure. The measured electrical impedance may be averaged over several seconds. In some exemplary methods, the measured electrical impedance of the pressure sensor is mapped against calibrated values to correlate the two parameters.

In a second exemplary method (or second exemplary stimulated mode), the device 10, 210 allows an instantaneous (or static pressure), such as an instantaneous compartment pressure, to be measured. The second exemplary method is also suitable for measuring trends in compartment pressure over extended periods. The second exemplary method is further suitable for determining pulse rates, and amplitudes of the cardiac variation.

On initialisation, the processor applies a stimulus, such as an electrical or ultrasound stimulus, to the sensor 22. The frequency of the stimulus is ramped in stages from a low frequency to a high frequency (or vice versa), and the resonant frequency, electrical impedance and/or capacitance of the sensor 22 determined. The applied frequency can be an AC frequency. However, pulsed or other waveforms are used in other embodiments.

The resonant frequency of the sensor 22 is indicative of (and dependent upon) the pressure differential ($P_{ext}$–$P_{bore}$). Therefore, it is possible to correlate the change in resonant frequency to the pressure differential ($P_{ext}$–$P_{bore}$) or external load pressure ($P_{ext}$). The resonant frequency of the pressure sensor can be calibrated by precisely machining the dimensions of the pressure sensor. For a precisely dimensioned pressure sensor, it will be possible to determine a known characteristic function that allows the direct correlation of the measured resonant frequency with a pressure differential.

In addition to the resonant frequency, the electrical impedance and/or capacitance of the pressure sensor can be indicative of the pressure differential in accordance with methods of the second exemplary stimulated mode.

In some embodiments the piezoelectric material used has a narrow resonance peak, or a high Q-factor, which helps to provide an increased sensitivity in the pressure measurement. In other embodiments, a low Q-factor is used to give a broad range of resonant frequency with good sensitivity. It may be preferable to use a Q-factor having an intermediate value. This compromise provides a broad based of resonance, whilst giving a higher resonance response.

In the first embodiment, the sensor has two resonance modes: (i) a thickness mode (parallel to the electric field); and (ii) a transverse mode (orthogonal to the electric field).

In the second exemplary method, the frequency of the stimulus applied to the sensor is ramped in stages over the frequency range, and the resonant peak detected through the electrical excitation. The lower and upper limits of the frequencies are selected by the user and may depend on the size and geometry of the sensor, and on the pressure differential values to be monitored. In some exemplary methods, the frequency range is between 0.1 and 30 MHz. In other exemplary methods, the frequency range is between 1 and 7 MHz. In other exemplary methods, the frequency range is between 16 and 22 MHz. The lower and upper limits of the frequency may be selected based on the pressure differential measured in the immediately preceding measurement. For example, the lower and upper limits of the frequency may be a localised ranged spanning the frequency that provided the maximum resonance of the immediately preceding measurement. For example, the localised range may be about ±5 Hz, ±2 MHz, ±1 MHz, or ±0.5 MHz around the frequency that provided the maximum resonance of the previous measurement.

In some exemplary methods, the measured resonant frequency is indicative of a mean static pressure. The measured resonant frequency may be a measured over several frequency cycles. For example, the resonant frequency may be measured over about 100 frequency cycles. In some exemplary methods, the resonant frequency is measured over a few milliseconds. In some exemplary methods, the sampling rate is up to about 1000 samples per second. The invention is not limited by the range of frequency used. In some exemplary methods, the resonant frequency of the pressure sensor is mapped against calibrated values to correlate the two parameters.

Figure 7A:
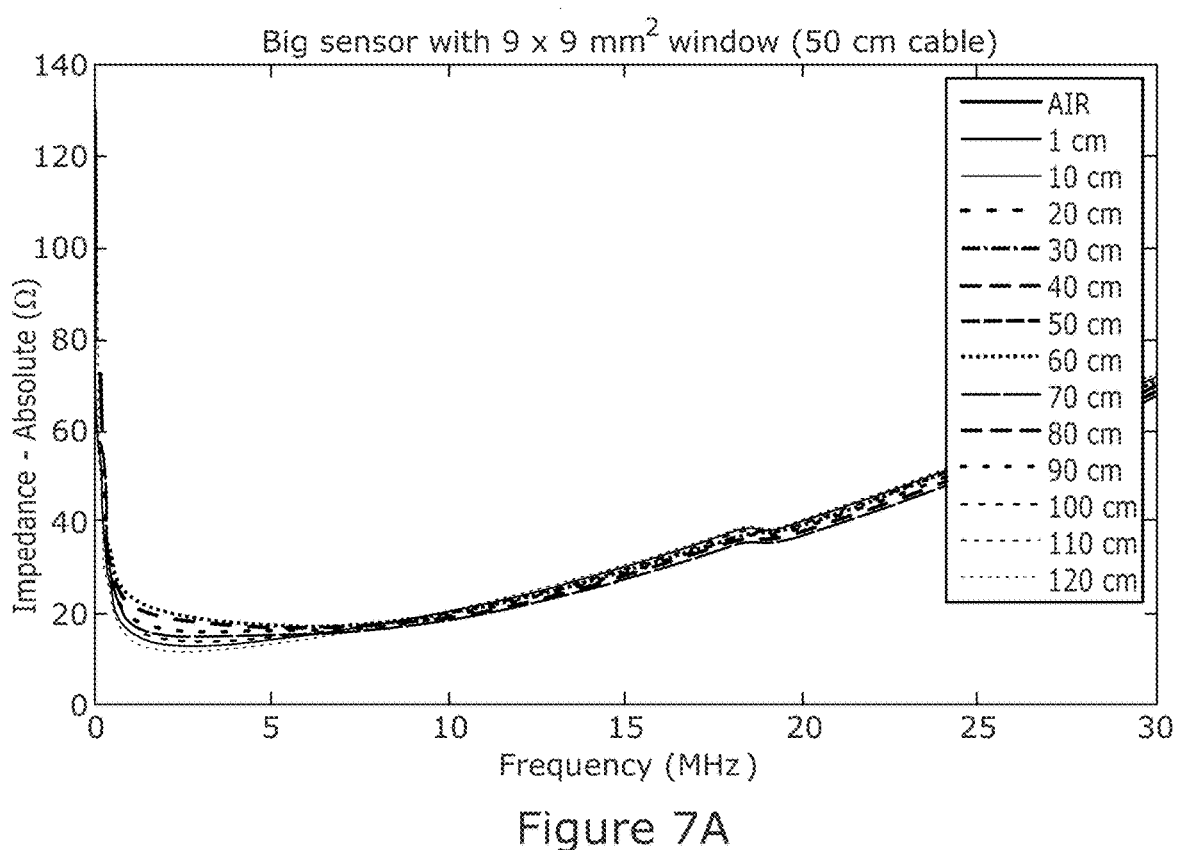
FIGS. 7A, 7B and 7C are graphs showing the change in impedance of a pressure sensor (of size 9 mm×9 mm) at different hydrostatic pressures.

FIG. 7A is a proof-of-concept example showing how the absolute impedance of a piezoelectric sensor, (with an active area of 9×9 mm$^2$), varied with applied frequency in a range of 0.1-30 MHz. The external load pressure in this example was varied using a column of water with a height from 0 cm to 120 cm (i.e. approximately 0-90 mmHg). In this example, the thickness mode has a resonant frequency around 18 MHz; and the transverse mode has a resonant frequency in the low MHz range.

The pressure sampling rate may be fast, for example, 10 samples per second. This allows rapid monitoring of changes in instantaneous pressure. For example, this beneficially allows a user (or clinician) to monitor changes in compartment pressure during specific tests, such as when a limb is raised. Again as an example, the pressure in a muscular compartment may increase if a limb is raised. Further, this beneficially allows instantaneous pressure measurements to be monitored during activity. Pressure measurement during activity allows a clinical diagnosis of exertional compartment syndrome.

In some exemplary methods, the measured resonant frequency is processed to provide information regarding dynamic pressure changes. For example, the calibrated baseline and/or the static compartment pressures may be removed from the measured response to provide dynamic pressure values. This allows pulse rates and amplitudes to be determined (with respect to the baseline value).

Alternatively the pressure sampling may be slow, for example, 1 sample per minute. This beneficially allows trends in static pressures to be monitored over an extended period of time. In one exemplary method, the pressure is monitored over a period of many hours. A slow sampling rate requires a lower power input, which also preserves battery life.

Figure 7B:
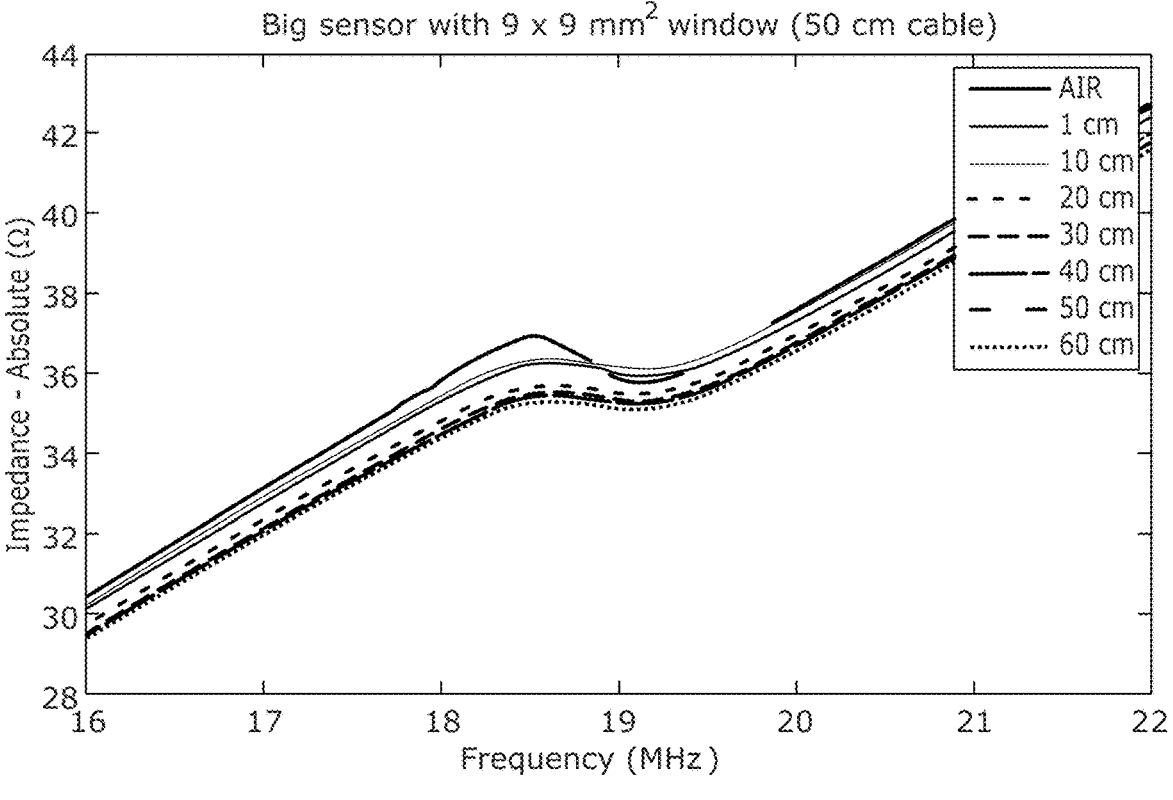

FIG. 7B is a magnified view of FIG. 7A between a range of 16 and 22 MHz with a column height from 0 cm to 60 cm (i.e. approximately 0-45 mmHg). These frequencies correspond to the resonant frequency of the thickness mode. As the load pressure increases, the impedance of the sensor decreases systematically.

Figure 7C:
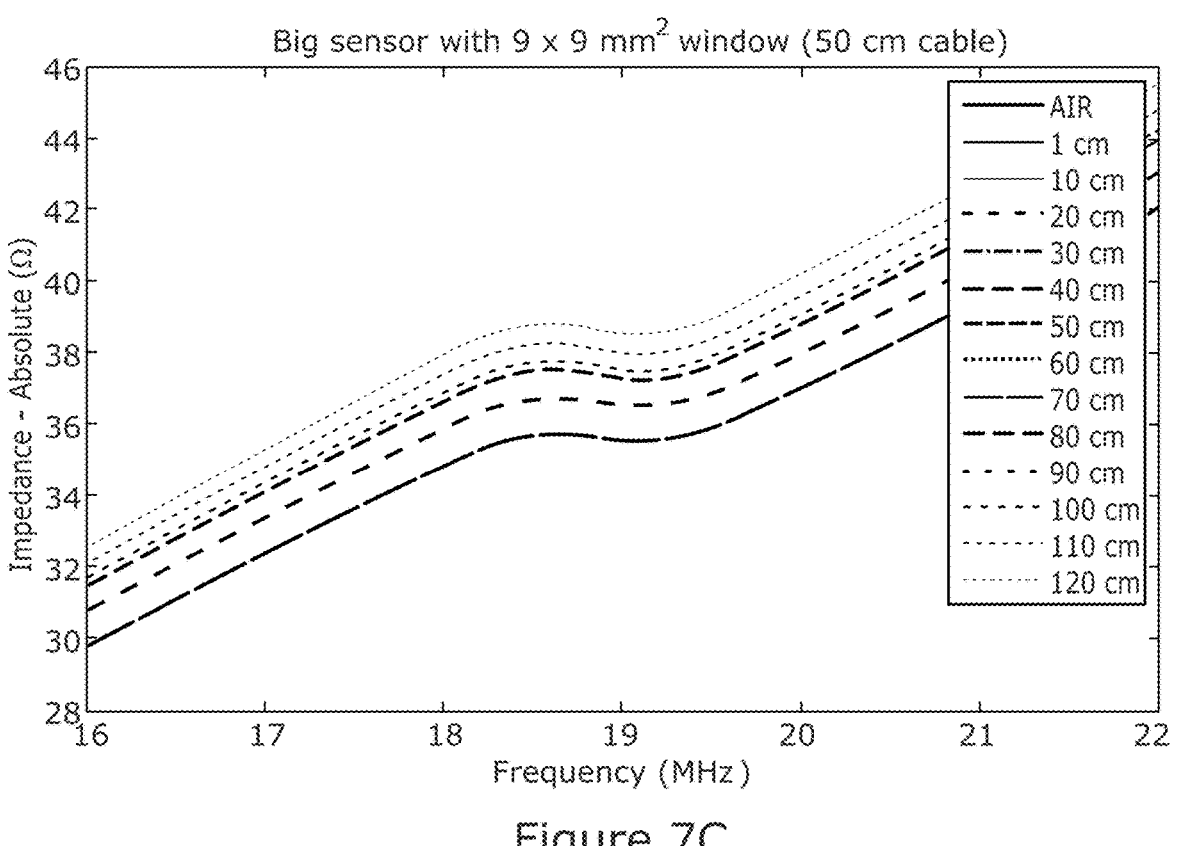

FIG. 7C is a magnified view of FIG. 7A between a range of 16 and 22 MHz with a column height from 70 to 120 cm (i.e. approximately 50-90 mmHg). These frequencies correspond to the resonant frequency of the thickness mode. As the load pressure increases (above 50 mmHg), the impedance of the sensor was found to increase. Without wishing to be bound by any theory or conjecture, it is believed that this is due to the large size of the sensor, and a change in contact area and electrode connection due to deformation under these high pressures. These effects were not observed for sensors of a small size.

Figure 8A:
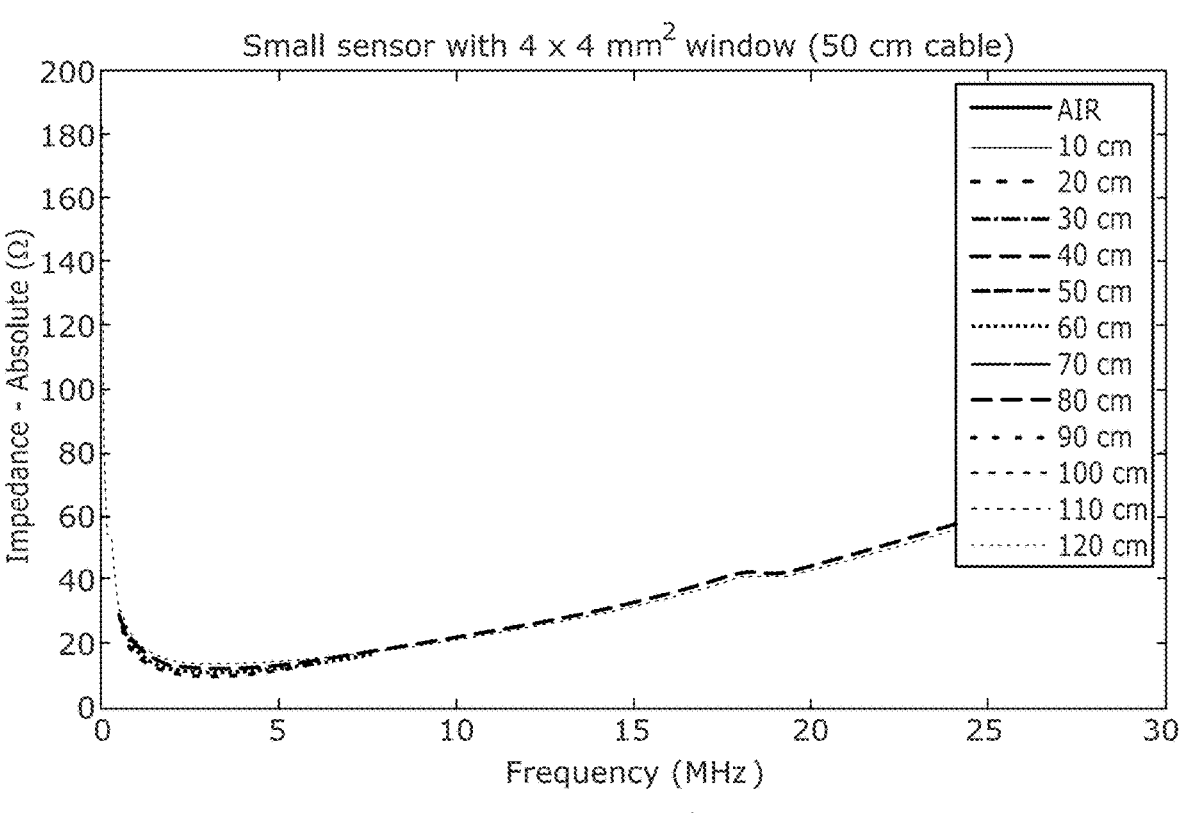
FIGS. 8A, 8B, 8C and 8D are graphs showing the change in impedance of a pressure sensor (of size 4 mm×4 mm) at different hydrostatic pressures.

FIG. 8A is a proof-of-concept example showing how the absolute impedance of a piezoelectric sensor (with an active area of 4×4 mm$^2$) varied with applied frequency in a range of 0.1-30 MHz. The external load pressure in this example was varied using a column of water with a height from 0 cm to 120 cm (i.e. approximately 0-90 mmHg). In this example, the thickness mode has a resonant frequency around 18 MHz; and the transverse mode has a resonant frequency in the low MHz range.

Figure 8B:
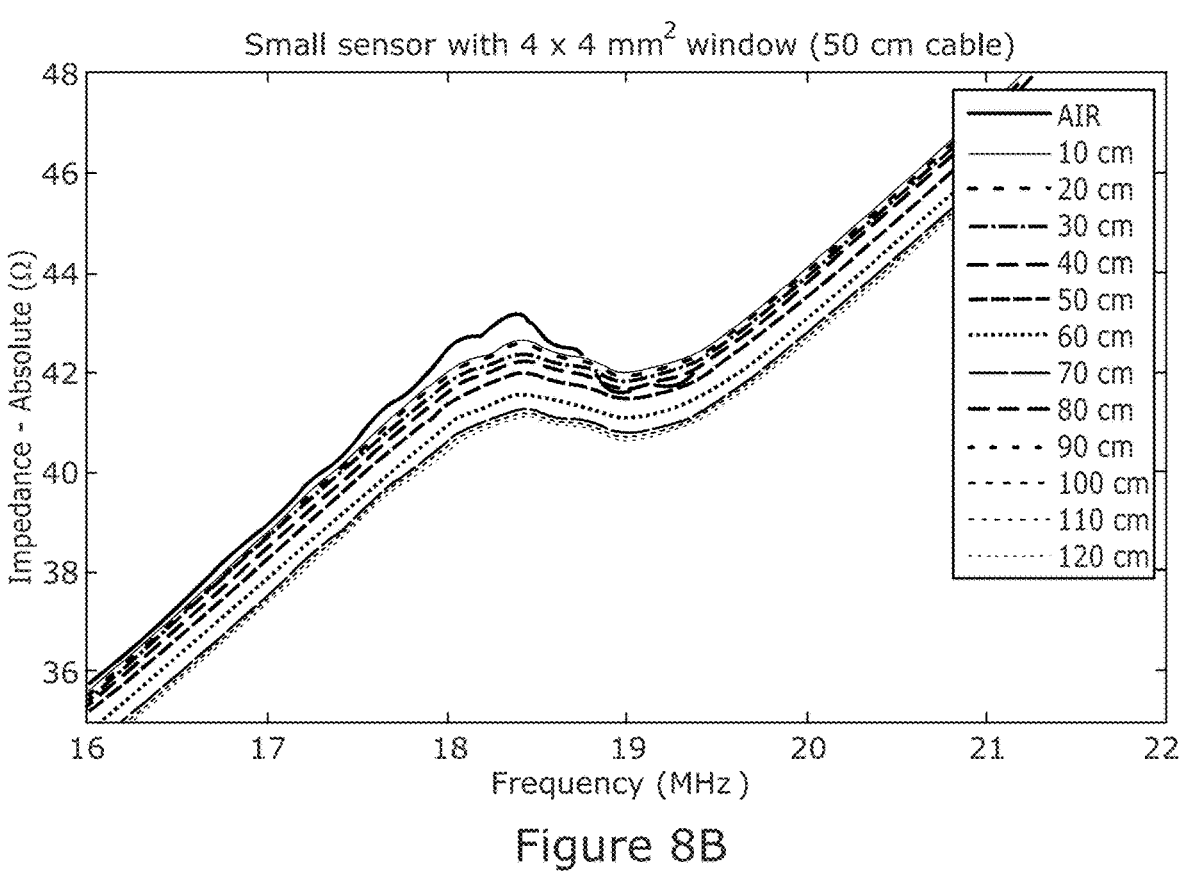
Figure 8C:
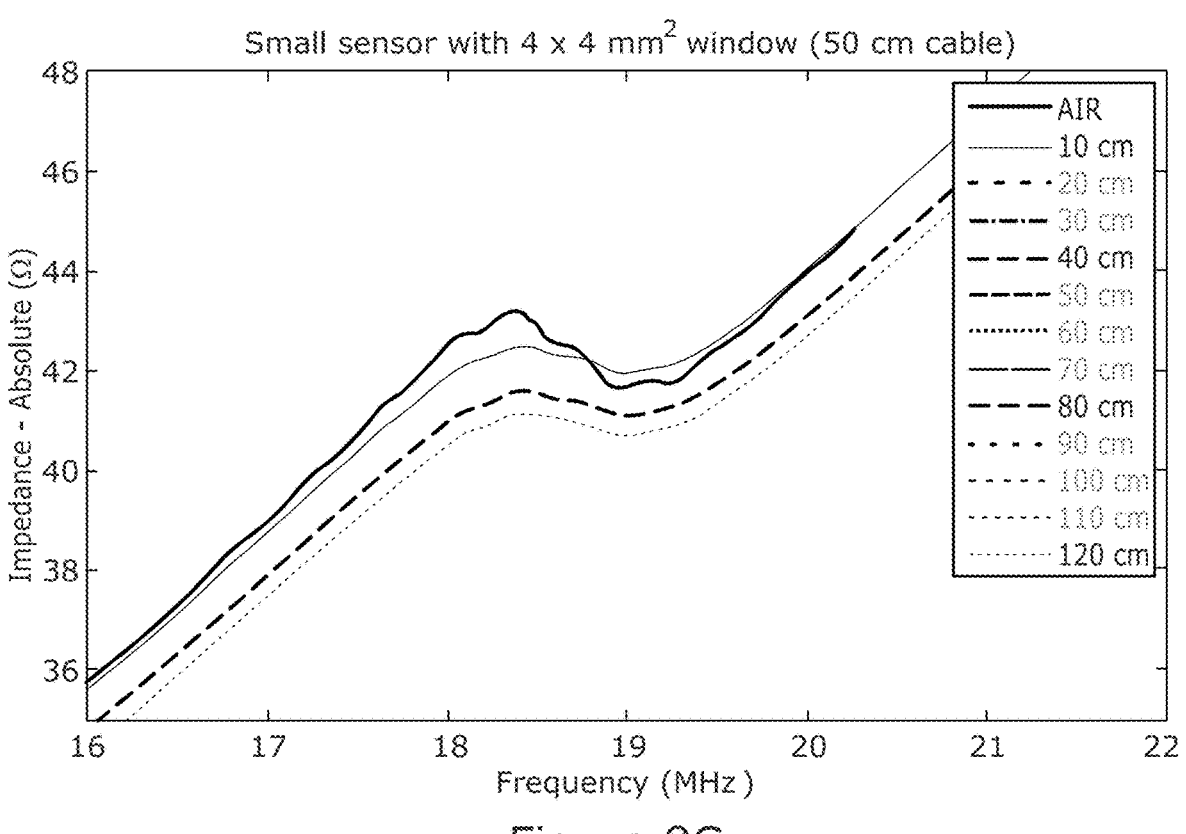

FIGS. 8B and 8C are magnified views of FIG. 8A between a (high) frequency range of 16 and 22 MHz across the same pressure range. These frequencies correspond to the resonant frequency of the thickness mode. As the load pressure was increased, the absolute impedance of the sensor decreased systematically.

Figure 8D:
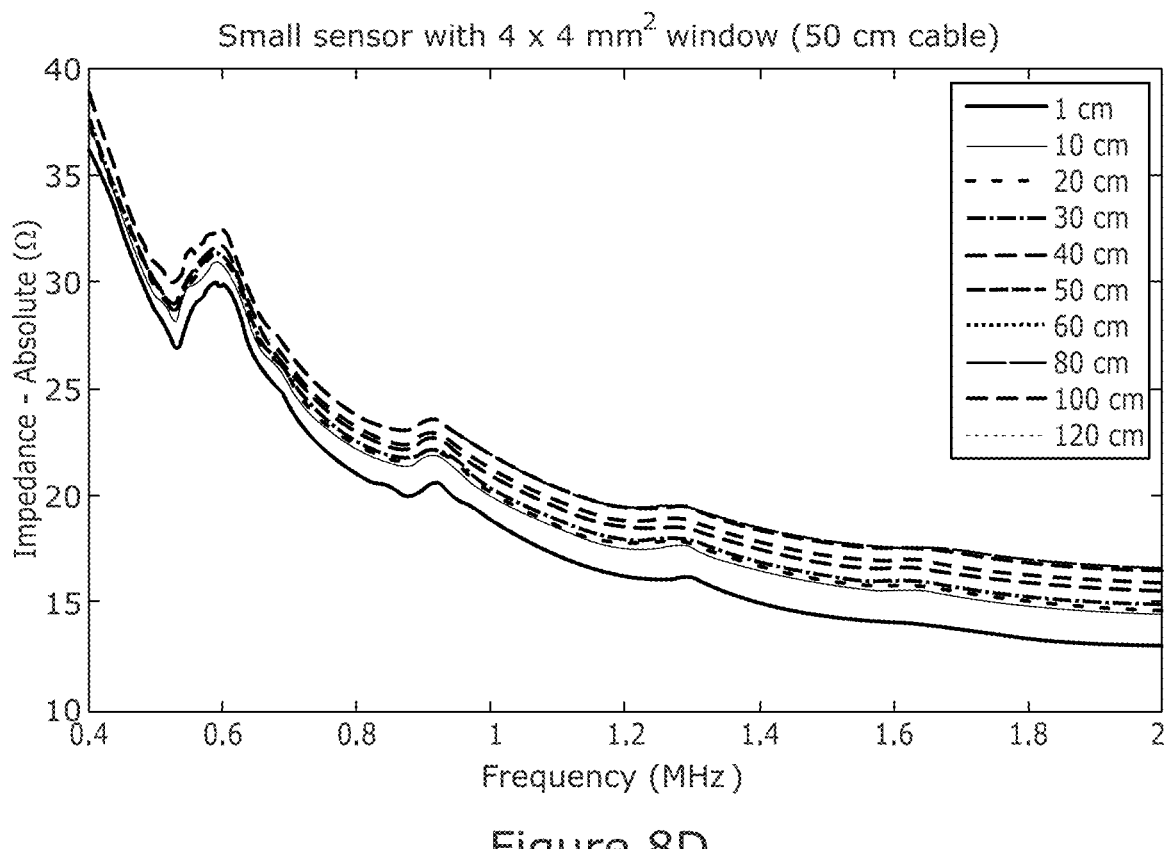

FIG. 8D is a magnified view of FIG. 8A between a (low) frequency range of 0.4 and 2 MHz. These frequencies correspond to the resonant frequency of the transverse mode. At this lower frequency, the absolute impedance increased systematically as the load pressure increased.

The results of the proof-of-concept experiments can be used to generate calibration curves for a device having the same sized active area.

In a third exemplary method (or passive operational mode), the device 10, 210 provides a dynamic pressure measurement. A dynamic pressure measurement is, for example, suitable for measuring delta pressure, arterial pulse rate, and for monitoring an attenuated and transformed cardiac cycle. In the third exemplary method, the sensor is not electrically (or ultrasonically) stimulated. However, the piezoelectric sensor 22 will provide a measurable response, such as an electrical or ultrasound signal, in response to a change in the pressure differential. In some exemplary methods, the electrical signal is measured as a change in impedance across the sensor 22. In the passive operational mode, there is no change in electrical signal if the pressure differential is a constant value. Therefore, the passive mode is not suitable for measuring static pressures. However, pulsatile pressure waves generated as a result of the cardiac cycle may be detected using the passive operational mode. The device is able to switch between the stimulated and passive modes.

The processor correlates a change in the measured signal with a change in pressure differential between the exterior of the needle ($P_{ext}$) and the internal bore ($P_{bore}$). In some exemplary methods, temporal data in the measured signal is used to determine the pulse rate.

In one exemplary method, the pressure sampling rate is 10 samples/second. This sampling rate is sufficiently fast to accurately record pulse rates of approximately 60 bpm (beats per minute). Faster sampling rates could be employed to record the pulsatile pressure waves in greater resolution. In some exemplary methods, the sampling rate is at least 10 times as fast as the pulse rate.

Figure 9:
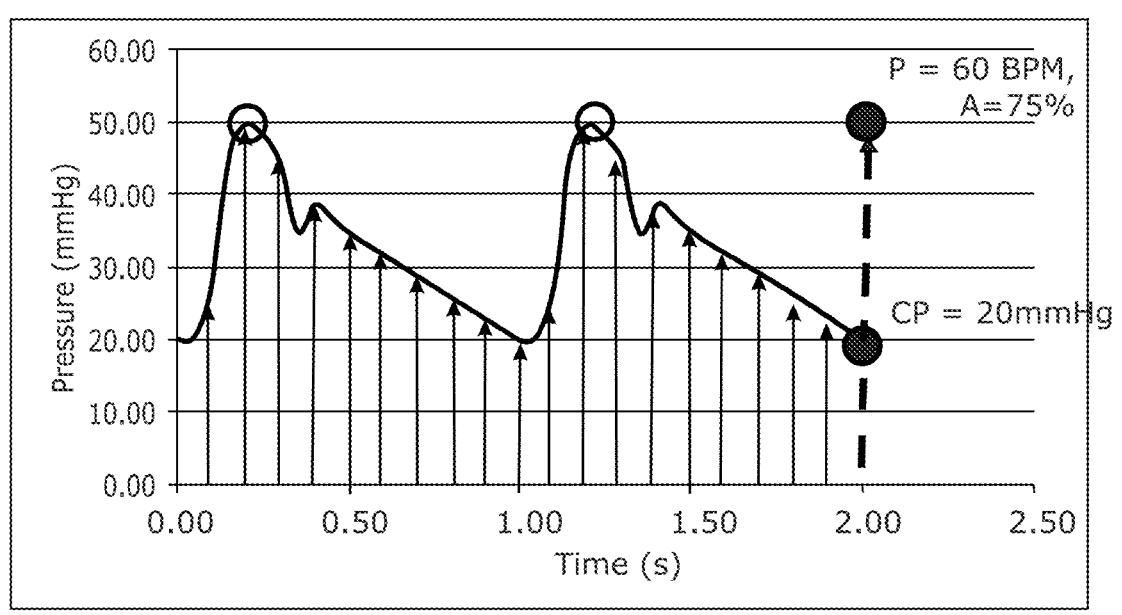
FIG. 9 is a graphical illustration of a pulsatile pressure wave.

FIG. 9 shows the pressure variation in a muscular compartment during two arterial pressure waves at a pulse rate of 60 bpm (beats per minute). The pressure is sampled at a rate of 10 samples per second. The peak pressure can be analysed to determine the pulse rate. The mean arterial pressure (MAP) may be determined using known formulae. The delta pressure and the compartment pressure may be determined using known formulae.

The first, second and/or third exemplary method may measure blood flow characteristics in terms of acoustic and pressure sensed signals which can be interpreted to yield information on the state of a blood vessel, for example, at the site of a cardiac procedure and in postoperative care to monitor internal blood pressure levels and conditions.

In a fourth exemplary method, the first, second, and/or third exemplary methods are alternated. That is, the electrical impedance (or resonant frequency) is measured alternately with measurements of changes in electrical impedance.

Figure 10:
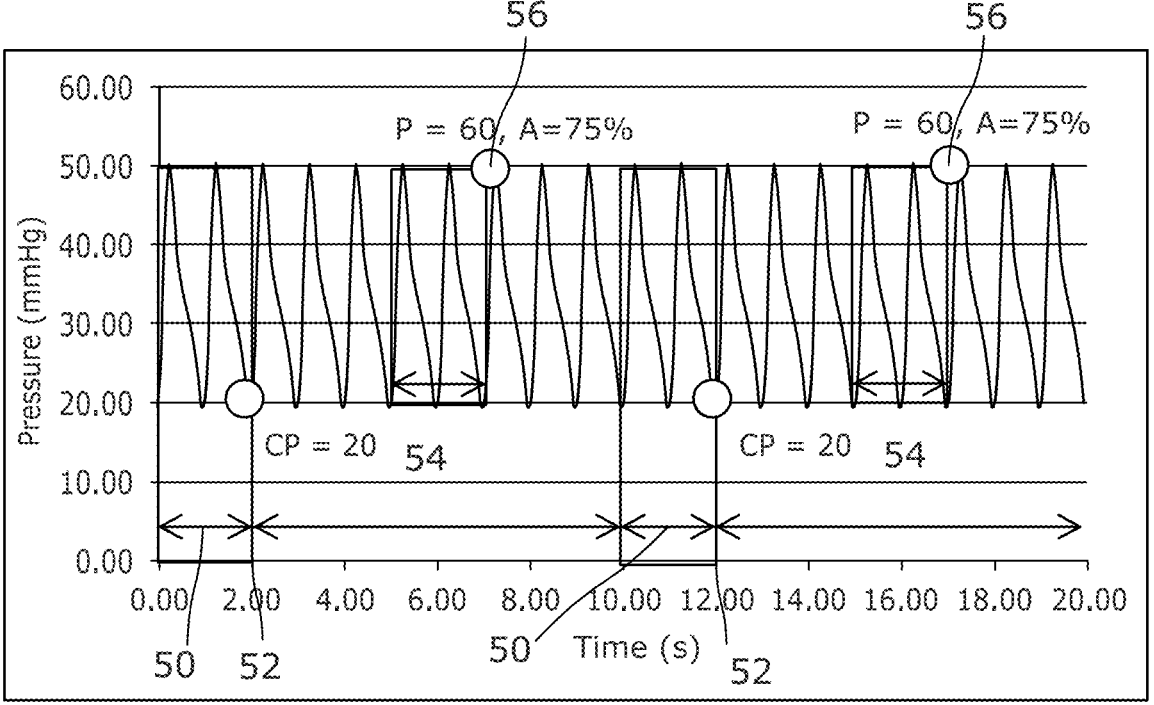
FIG. 10 is a graphical illustration of the fourth exemplary method.

FIG. 10 shows the pressure variation in a muscular compartment at a pulse rate of 60 bpm (beats per minute). The pressure sensor is electrically stimulated during the period indicated by reference numeral 50. The electrical impedance (or resonant frequency) of the pressure sensor is measured at 52. The electrical impedance (or resonant frequency) is measured at a sampling rate of 6 samples per minute. The sample duration is 2 s. That is, the pressure sensor receives electrical stimulation during the electrical impedance (or resonant frequency) measurement for a duration of 2 s.

The device is not electrically (or ultrasonically) stimulated during the period indicated by reference numeral 54. Whilst the pressure sensor is not being electrically (or ultrasonically) stimulated, the device can measure dynamic changes in pressure differential. Changes in electrical resistance of the pressure sensor are measured at 56. For example, changes in electrical impedance of the pressure sensor may be measured in accordance with the third exemplary method. This can provide clinical information such as pulse rate.

The peak pressure can be analysed to determine the pulse rate. The mean arterial pressure (MAP) and the delta pressure may be determined using known formulae. Alternating between first, second and/or third exemplary methods reduces power consumption and helps to preserve battery life.

The fourth exemplary method may measure blood flow characteristics in terms of acoustic and pressure sensed signals which can be interpreted to yield information on the state of a blood vessel, for example, at the site of a cardiac procedure and in postoperative care to monitor internal blood pressure levels and conditions.

In some exemplary methods, the device delays or suspends pressure measurements during needle insertion into a body.

In some embodiments, the device is switchable between the first, second, third, and/or fourth exemplary methods. In some embodiments, the sampling rate is user adjustable.

In some embodiments, the tube comprises a flexible tube. The flexible tube may be hollow, comprising an internal bore, a closed first end (or tip) and an open second end, as described in relation to previous embodiments. The flexible tube may have any cross-sectional geometry. The flexible tube may comprise a pressure sensor as described in previous embodiments. In some embodiments, the flexible tube (or needle) has a blunt end. The flexible tube may be positioned at a location in a body for pressure measurement during a surgical procedure or via a cannula, rather than being inserted into a body by penetrating body tissue. Embodiments incorporating a flexible tube have applications in, for example, measuring post-operative intracranial pressure; and monitoring arterial pressure at locations along a blood vessel to indicate arterial narrowing. Identifying arterial narrowing provides an indication that angioplasty or similar treatments may be required.

In some embodiments, the pressure sensor provides the closure for the closed first end.

In some embodiments, the pressure sensor comprises at least two pressure sensors. For example, the pressure sensor may be a dual-segment hybrid sensor. The first pressure sensor is operated in the first and/or second exemplary method, and the second pressure sensor is operated in the third exemplary method.

In some embodiments, an insertion site guide is used to indicate the appropriate needle insertion site. The insertion site guide may comprise a wearable sleeve or sheet for position over the body. The insertion site guide may be made from a transparent, flexible material. The insertion site guide may comprise an indication of the location of muscular compartments. Correct positioning of the insertion site guide may be achieved using reference points provided on the insertion site guide. The insertion site guide may provide an indication of the necessary needle penetration depth for a muscular compartment. The insertion site guide beneficially facilitates insertion of the needle into the correct location and at the correct penetration depth to measure the pressure differential value of interest. The insertion site guide also beneficially facilitates insertion of the needle at the same location, which reduces experimental variation during repeated pressure measurements.

Whilst the present invention has been described above in relation to medical applications, in particular the measurement of a compartment pressure and intracranial pressure, embodiments of the device and associated methods of use are suitable for measuring pressure differentials in other medical applications, such as bone marrow investigations, and in non-medical applications alike. Non-medical applications of the present invention include, but are not limited to, measuring a pressure differential: in a pressurised chamber, such as a tyre; in a sealed chamber, such as a sealed reaction vessel; or in a low pressure chamber, such as a vacuum chamber.

The invention claimed is:

1. A device for measuring a pressure differential comprising:
    a tube comprising a closed insertion portion for insertion into a body, the closed insertion portion having an insertion end, and an internal bore which is in communication with ambient pressure via an opening in the tube;
    at least one pressure sensor located in or on the closed insertion portion, the at least one pressure sensor comprising an internally facing region which is in communication with the internal bore and an externally facing region which is in communication with an exterior of the tube; and
    a processor configured to provide a stimulus to mechanically excite the at least one pressure sensor so that when the stimulus is provided, the at least one pressure sensor provides a measurable resonant response, wherein the processor correlates the measurable resonant response with the pressure differential between the exterior of the tube and the internal bore.

2. The device according to claim 1, in which the at least one pressure sensor is located proximal to the insertion end.

3. The device according to claim 1, comprising a plurality of pressure sensors, in which at least two of the plurality of pressure sensors have different resonant frequencies at a same pressure differential.

4. The device according to claim 1, in which the externally facing region of the at least one pressure sensor is aligned with the exterior of the tube.

5. The device according to claim 1, in which the closed insertion portion comprises at least one sealed aperture, in which each aperture is sealed by at least one pressure sensor.

6. The device according to claim 1, in which the at least one pressure sensor comprises an electro-mechanical or micro-electromechanical (MEMs) material.

7. The device according to claim 1, in which the at least one pressure sensor comprises a piezoelectric pressure sensor or an electro-capacitive pressure sensor.

8. The device according to claim 1, in which the stimulus comprises an electrical stimulus.

9. The device according to claim 1, in which the measurable resonant response is an electrical response.

10. The device according to claim 1, in which the measurable resonant response is indicative of an electrical impedance of the at least one pressure sensor.

11. The device according to claim 1, in which the measurable resonant response is indicative of a resonant frequency of the at least one pressure sensor.

12. The device according to claim 1, in which the measurable resonant response is indicative of a change in pressure differential between the exterior of the tube and the internal bore.

13. The device according to claim 1, further comprising a user-holdable portion which is in connection with the tube, in which the internal bore is in communication with ambient pressure via the user-holdable portion.

14. The device according to claim 13 in which the user-holdable portion comprises a penetration restraint mechanism operable to limit a penetration depth of the tube.

15. The device according to claim 1, in which the tube is a needle.

16. A method of measuring a pressure differential using the device according to claim 1, the method comprising the steps of:

providing a stimulus to mechanically excite the at least one pressure sensor so that the pressure sensor provides a measurable resonant response;

measuring the measurable resonant response, wherein the measurable resonant response is indicative of the pressure differential between the exterior of the tube and the internal bore, the internal bore being in communication with ambient pressure via the opening in the tube; and correlating the measurable resonant response with the pressure differential between the exterior of the tube and the internal bore.

17. The method according to claim 16 further comprising the step of calibrating the device, the step of calibrating the device comprising the sub-steps of:

providing a stimulus to mechanically excite the at least one pressure sensor whilst maintaining the externally facing region of the at least one pressure sensor at ambient pressure so that the at least one pressure sensor provides a measurable resonant calibration response indicative of the pressure differential between the exterior of the tube and the internal bore;

measuring the measurable resonant calibration response; and correlating the measured resonant calibration response with a pressure differential of zero.

18. The method according to claim 16 in which the stimulus is an alternating and/or pulsed electrical stimulus.

19. The method according to claim 16 in which a frequency of the stimulus is varied.

20. The method according to claim 16 in which a frequency of the stimulus is increased or decreased from a first frequency to a second frequency.

* * * * *